US012678573B2

(12) United States Patent
Lettman et al.

(10) Patent No.: US 12,678,573 B2
(45) Date of Patent: Jul. 14, 2026

(54) NASAL SPRAY MEDICAMENT TRAINING DEVICE

(71) Applicant: NOBLE INTERNATIONAL, LLC, Orlando, FL (US)

(72) Inventors: Jeffery A. Lettman, Orlando, FL (US); Joshua Hopkins, Casselberry, FL (US); Tingting Liu, Orlando, FL (US)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 1074 days.

(21) Appl. No.: 17/639,072

(22) PCT Filed: Aug. 31, 2020

(86) PCT No.: PCT/US2020/048756
§ 371 (c)(1),
(2) Date: Feb. 28, 2022

(87) PCT Pub. No.: WO2021/042037
PCT Pub. Date: Mar. 4, 2021

(65) Prior Publication Data
US 2022/0273893 A1     Sep. 1, 2022

Related U.S. Application Data

(60) Provisional application No. 62/893,887, filed on Aug. 30, 2019.

(51) Int. Cl.
A61M 15/08 (2006.01)
G09B 23/28 (2006.01)

(52) U.S. Cl.
CPC ............. A61M 15/08 (2013.01); G09B 23/28 (2013.01); A61M 2205/276 (2013.01)

(58) Field of Classification Search
CPC .............. A61M 15/00; A61M 15/0001; A61M 15/0081; A61M 15/08; A61M 11/00;
(Continued)

(56) References Cited

U.S. PATENT DOCUMENTS 2,607,626 A     8/1952   Tucci
4,475,905 A  *  10/1984  Himmelstrup .... A61M 5/31551
604/263
(Continued)

FOREIGN PATENT DOCUMENTS

CN        103561873  A  *   2/2014   .......... A61M 11/007
WO     2019142007  A1      7/2019
WO     2021042037  A2      3/2021

OTHER PUBLICATIONS

CN-103561873-A machine translation accessed Apr. 4, 2025 (Year: 2025).*
(Continued)

*Primary Examiner* — Victoria Murphy
*Assistant Examiner* — Kelsey Rhee
(74) *Attorney, Agent, or Firm* — Timothy H. Van Dyke; Wolter Van Dyke Davis, PLLC

(57) ABSTRACT

In at least one embodiment, there is provided a nasal drug delivery training device for training a subject to deliver medicament to a nasal airway, including a pre-use position and a post-use position, a housing comprising a cavity, a proximal end, and a distal end, and a nasal interfacing portion near the proximal end. The device includes a plunger movable relative to the housing, said plunger having a retracted position, and an extended position, and a plunger biasing member associated with the plunger for resetting the plunger to the extended position post use, wherein move-
(Continued)

ment of the plunger toward the proximal end of the housing simulates delivery of medicament to a nasal airway with a nasal drug delivery device.

21 Claims, 23 Drawing Sheets

(58) Field of Classification Search
CPC .... A61M 11/007; A61M 11/06; A61M 5/178; A61M 5/20; A61M 5/31543; B05B 11/1059; B05B 11/0027; B05B 11/1091
See application file for complete search history.

(56) References Cited

U.S. PATENT DOCUMENTS

| | | | |
|---|---|---|---|
| 5,431,155 A * | 7/1995 | Marelli ................. | B05B 11/007 128/200.22 |
| 6,189,739 B1 | 2/2001 | von Schuckmann | |
| 2005/0066961 A1 * | 3/2005 | Rand ................. | A61M 15/0068 128/200.14 |
| 2005/0098172 A1 * | 5/2005 | Anderson ........... | B05B 11/1091 128/200.14 |
| 2008/0249459 A1 * | 10/2008 | Godfrey .............. | A61M 15/009 222/162 |
| 2009/0236445 A1 | 9/2009 | Lintern et al. | |
| 2010/0095957 A1 | 4/2010 | Corbacho | |
| 2012/0193377 A1 | 8/2012 | Wong | |
| 2015/0183571 A1 | 7/2015 | Anderson et al. | |
| 2016/0293058 A1 | 10/2016 | Gaillot et al. | |
| 2016/0335920 A1 | 11/2016 | Bendek et al. | |
| 2021/0049930 A1 * | 2/2021 | Mortimer ............. | A61M 11/007 |

OTHER PUBLICATIONS

PCT/US2020/048756, PCT Search Report & Written Opinion mailed Feb. 11, 2021, 28 pages.

Aptar Pharma: Leader in Innovative Drug Delivery Systems, Downloaded from Internet Jun. 12, 2019, 3 pages.

Consort Medical, Nasal Spray Device Unidose Xtra, Downloaded from Internet Jun. 12, 2019, 5 pages.

Supplementary EP Search Report, EP20847646, Aug. 24, 2023, 2 pages.

* cited by examiner

200

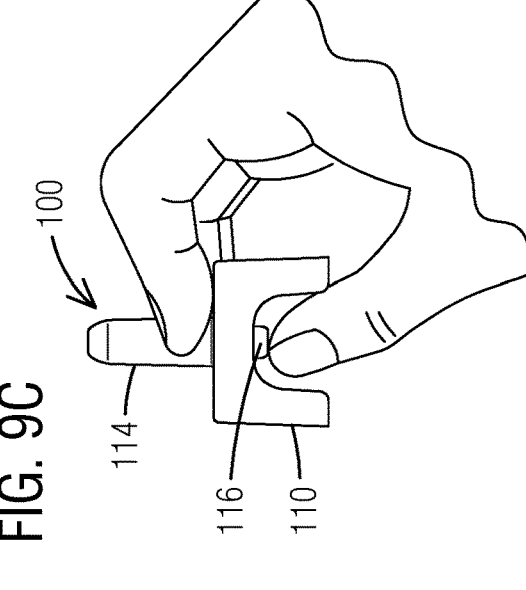
FIG. 9C
FIG. 9B
FIG. 9E
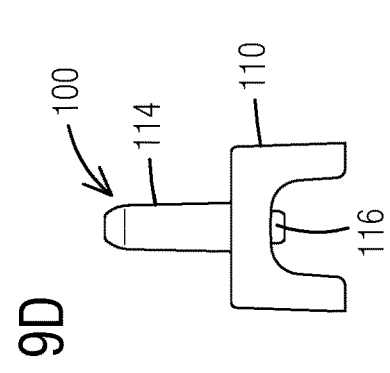
FIG. 9D
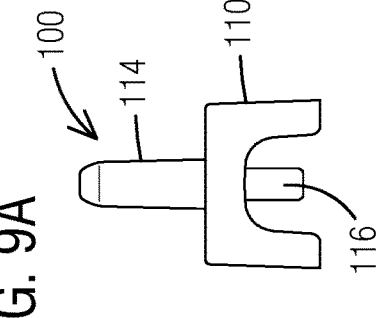
FIG. 9A

Before Use

1st Activation

F
Push Actuator

Release Thumb

2nd Activation

F
Push Actuator

After 2nd Dose

Release Thumb

Reset

Turn Nasal Tip
to Reset

FIG. 14C
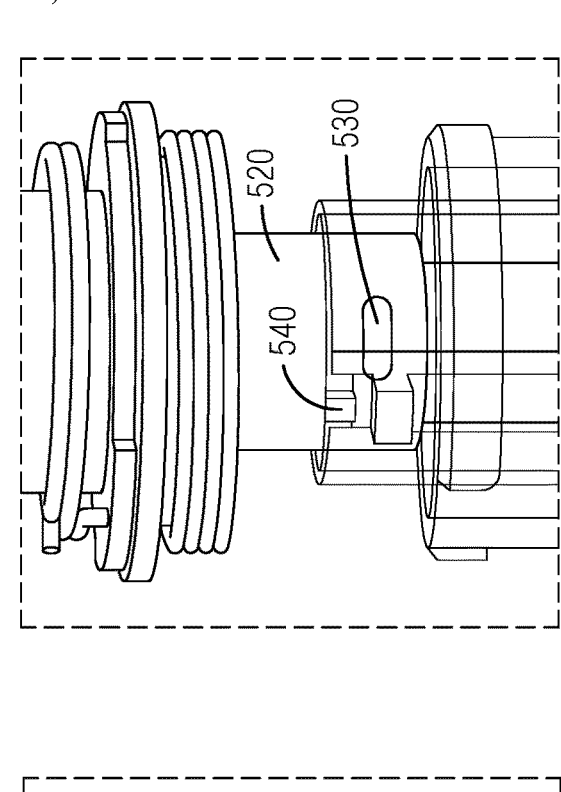
FIG. 14B
FIG. 14A
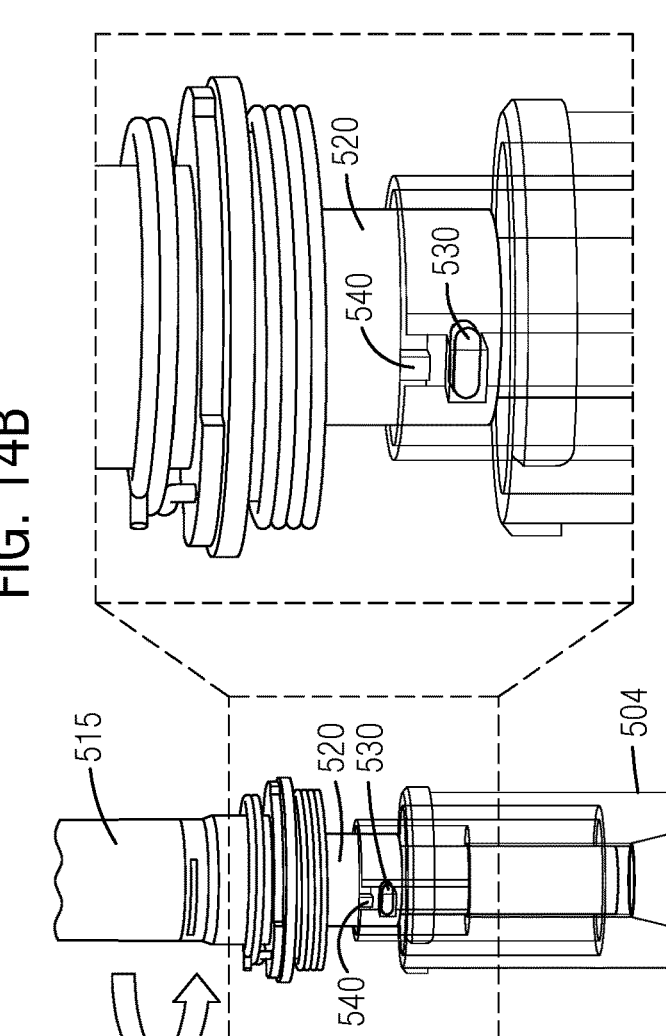

FIG. 14E
FIG. 14D
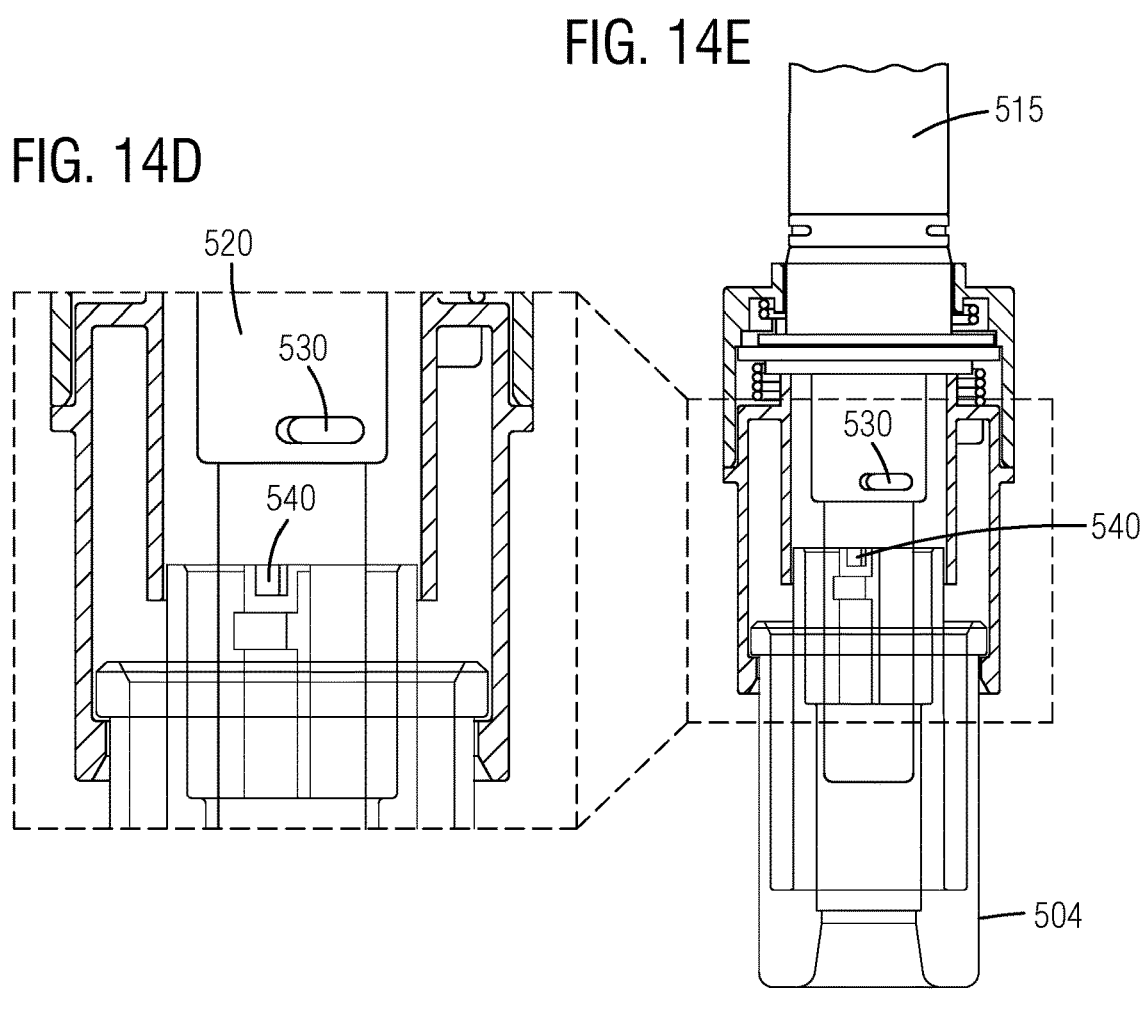
FIG. 15A
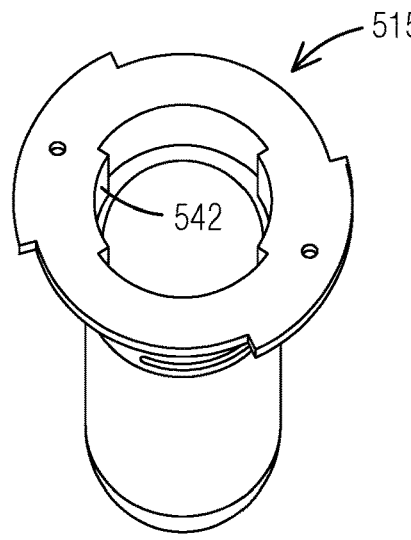
FIG. 15B
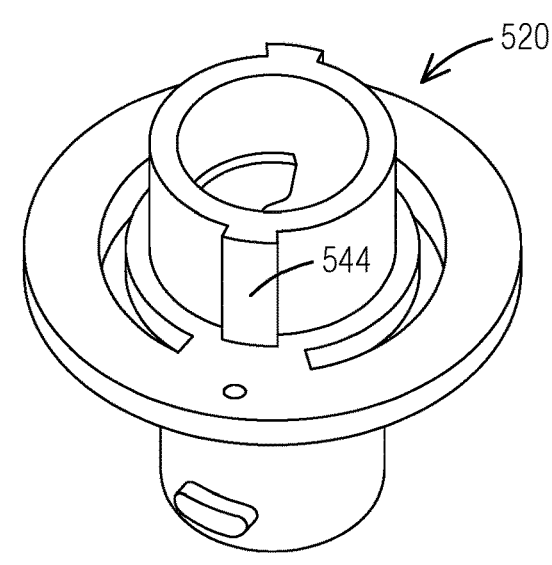

NASAL SPRAY MEDICAMENT TRAINING DEVICE

BACKGROUND

Delivery of medicament through the nasal delivery route can be used to treat a number of different diseases and conditions, or to relieve symptoms associated therewith. Such diseases and conditions include allergic rhinitis, nasal congestion, anaphylaxis, bronchitis, common colds, chronic conditions such as Alzheimer's, Parkinson's, or treatment for depression. Certain therapies would benefit from nasal delivery of medicament, including treatment for epilepsy and migraine treatment, treatments for seizures, or treatment for an overdose. Moreover, the nasal delivery route is often used for administration of vaccines, immunotherapies and/or anti-viral medications. Some medications have numerous steps which must be followed in a precise manner in order to receive an accurate dosage of the medication. Certain medications must be given only once, others multiple times to be effective. Some nasal delivery medicaments require precise timing of multiple steps to be performed in conjunction with one another, or precise force used and speed achieved during actuation to deliver a correct dose of medicament. Without proper training, these devices can be extremely difficult to use and can create a sense of anxiety in a user. Moreover, as some medicaments require multiple doses for effectivity, practice using a device that delivers multiple doses increases patient cooperation and compliance.

For example, in cases of anaphylaxis, for example, persons at risk are required to carry two epinephrine auto-injectors at all times as up to 30% of patients who develop anaphylaxis require a second dose of epinephrine to control symptoms. However, patients rarely carry two epinephrine auto-injectors. Moreover, patients are rarely used to delivering medicament twice. Therefore, patient compliance requires practice using a training device that simulates a drug delivery device. Typically drug delivery device developers focus on ease of use of a device in development, not ease of learning. Learning to correctly use a device is the most relevant and most critical factor in preventing or reducing patient errors during use of the medicament delivery device, particularly via the nasal route.

BRIEF DESCRIPTION OF DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIGS. 9A-9E are examples of steps of a method of using a nasal drug delivery training device according to one embodiment.

FIGS. 14A-14E show various views of reset of the actuator portion during the nasal drug delivery training device reset shown in FIGS. 11-13.

FIGS. 15A-15B show a portion of the nasal interfacing portion protrusion and the locking member, and the interactivity between these components.

DETAILED DESCRIPTION

Figure 1A:
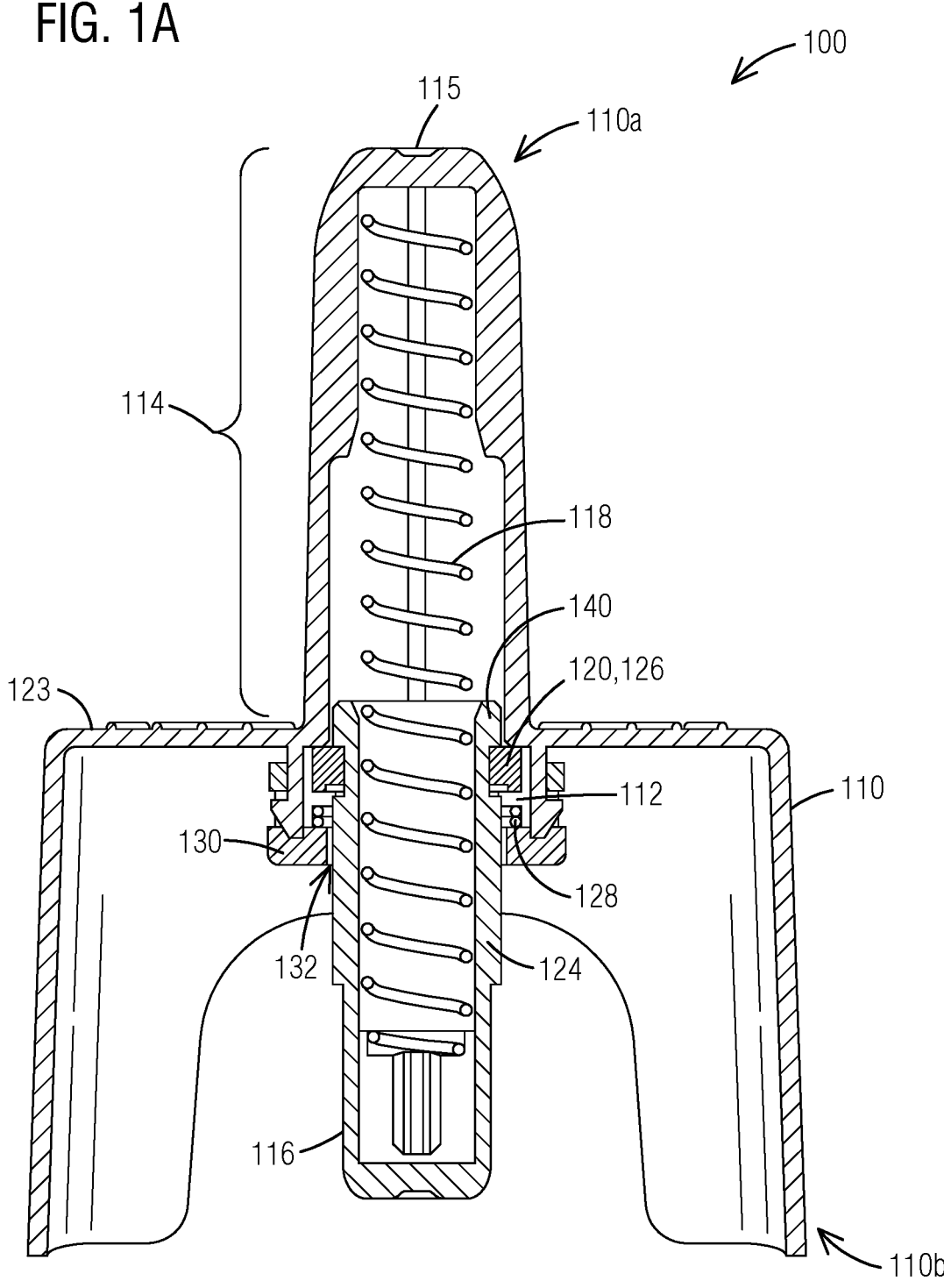
FIG. 1A is a cross sectional view of an embodiment of a nasal drug delivery training device.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

The term "medicament" as used in describing the various embodiments of this invention includes an injectable liquid medicine, medication, drug, pharmaceutical, prescriptive, agent, antidote, anti-venom, hormone, stimulant, vasodilator, anesthetic, nutritional supplement, vitamin and/or mineral compound, saline solution, biological, organic compound, genetically and/or chemically modified protein and/or nucleic acids, or other liquid that is adapted to be injected into the tissue of a subject.

The term associated or association, as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output.

As used herein, the terms "subject", "user" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human of the female gender.

The term "an effective amount" means an amount of an agonist or antagonist satiety factor or compositions comprising thereof that when, administered to a subject for treating a disease is sufficient to effect such treatment for the disease. An effective amount can vary depending on, inter alia, the satiety factor used, the disease and its severity and the age, weight, etc. of the subject to be treated.

"Preventing" or "prevention" refers to a reduction in the risk of acquiring a disease or disorder (i.e., causing at least one of the clinical symptoms of the disease not to develop in a subject that may be exposed to or predisposed to the disease but does not yet experience or display symptoms of the disease). Preferably, prevention refers to the use of a compound or composition in a subject not yet affected by the disease or disorder or not yet exhibiting a symptom of the disease or disorder, for instance a subject not yet infected or not yet exhibiting the symptoms of infection.

"Treating" or "treatment" of any disease or disorder refers, in one embodiment, to ameliorating the disease or disorder (i.e., arresting or reducing the development of the disease or at least one of the clinical symptoms thereof) that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. For example "a sensor" may denote the presence of at least one sensor; however, multiple sensors may be contemplated unless otherwise specifically stated. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

The term "sensor" or "sensors" as used herein may include but are not limited to, light sensors, fluid flow rate sensors, strain gauge sensors, temperature sensors, pressure sensors, tilt sensors, force sensors, level sensors, contact sensors, photoelectric sensors, magnetic sensors, ultrasonic sensors, electrochemical sensors, acceleration sensors, moisture sensors, humidity sensors, speed sensors, inductive sensors, capacitive sensors, and orientation sensors. Some of these sensors may require a supply of voltage. The medicament system may include one or more of the sensors described herein, for example, a contact sensor may be used to detect removal or placement of the smart device onto the medicament device, for example, or removal or placement of the medicament device onto the user, in another example. In a further example, two or more contact sensors, more preferably thee contact sensors may be used to detect perpendicularity of the medicament device relative to a target area of a patient. An example of an inductive sensor includes material embedded in or associated with the medicament device, wherein said embedded or associated material proportionally changes the magnetic field of the inductive sensor which may be associated with or embedded in the smart device, in one non-limiting example, depending on its distance away from the inductive sensor. The sensor then outputs a variable electrical signal based on the distance between the embedded or associated material and the inductive sensor.

The tactile or vibration component may include a vibration system, which provides a vibratory sensation. In one embodiment, this vibrator system may include a motor, in a non-limiting example a small DC motor, a gear and a weight. The weight may be mounted off-center on the gear, such that when the motor spins, the gear/weight combination at 100 to 150 rpm for example, the off-center mounting creates a vibration. In another embodiment, a linear transducer may be used. In a further example, an eccentric motor can be used to provide an oscillation or vibration.

Overview

Embodiments of the device include a nasal drug delivery training device for addressing many common errors in patient use of nasal drug delivery devices. Some of these errors include failure to actuate the device with sufficient force to deliver an effective amount of medicament, or accidental actuation of the device prior to intended actuation. Other errors include use of sufficient force to satisfy actuation of the device, but insufficient force to quickly depress the plunger. Intimidation in self -administering medication, particularly via the nasal route plays a large part in errors occurring during use of the nasal drug delivery devices. Additionally, when a nasal drug delivery device is used to administer medicament to a patient by another, it may be difficult to determine whether the dose of medicament is adequately delivered to the patient. Use of a training device to facilitate correct use of the drug delivery device will enhance compliance and ensure accurate dosage of medicament received.

Smart Technology

In addition to increasing confidence in self-administration in users by practicing with a training device, the inventors have identified additional benefits associated with multi-sensory learning using a medicament training device. It has been discovered that multi-sensory learning establishes multiple pathways in separate areas in the brain and ultimately results in a highly effective learning experience. However, in order to gain the maximum benefit from multi-sensory learning devices, the sources of stimuli must be in close proximity to one another; the sources of stimuli must be synchronous; the stimuli must be congruous semantically, otherwise the superior colliculus (area of the brain located in the midbrain known for integrating multiple sources of information) will segregate the stimuli instead of integrate them; and finally, the use of extraneous materials must be limited. With knowledge of the essential factors in multi-sensory learning and incorporation of the multi-sensory learning features into a training device, the inventors have developed a novel, cutting-edge medicament training device for a nasal drug delivery device.

Exemplary embodiments of the training device can be implemented to educate users on the proper operation and usage of a drug delivery device. The training device can be used to make prospective and current users of drug delivery devices feel more comfortable and confident in self-administration (or administration to others) of medicaments and can help users understand the proper steps of medicament delivery. Exemplary embodiments of the training device can be used by a user before the user administers a medication by way of, for example, a nasal drug delivery device.

The training device takes advantage of the multisensory learning capabilities of the human brain. As such, the training device provides the means to stimulate primarily the visual, auditory and somatic systems of the human nervous system.

Visual stimuli or feedback (visual output) can be generated mechanically or electronically. An example of a mechanically generated visual stimulus is a plunger moving relative to a housing in a device. An example of an electronically generated visual stimulus is one or more LED's blinking, an LCD display showing an icon, or key steps in the process of administration being highlighted on a screen in the order required for proper administration of medicament, in non-limiting examples. A visual output as disclosed herein includes but is not limited to a light, a display, a colorimetric display system, a change in position of the device or components of the device relative to one another, or any other type of visual cue to the user of the device. The visual output is associated with the training device, and may be disposed on the device itself, or provided in connection with the device by wired or wireless connection.

Additional visual outputs that may be incorporated into the device herein may include display devices having one or more layers of material having a light transmission region, a unit of information to be highlighted, and a light blocking region; and a backlight unit having a flexible, planar waveguide body, a light source configured to direct light into the waveguide body, and at least one light director associated with a portion of the waveguide body so as to direct light transversely to a plane of the waveguide body. The directed light travels through the light transmission region, and the directed light is directed toward the unit of information to be highlighted as provided in International Application No. PCT/US11/26976 and U.S. National Stage application Ser. No. 13/582,560 which claim the benefit of U.S. Provisional Application Ser. No. 61/310,081, which are incorporated by reference in their entireties herein. The unit or units of information to be highlighted may include the stepwise instructions for administering the medicament to a user and may also provide the duration of each step by way of highlighting each step for a predetermined amount of time such that the user can follow the precise timing of each step in the sequence.

Auditory stimuli or feedback (audio output) can also be generated mechanically or electronically. An example of a mechanically generated auditory stimulus is the "click" that can be heard if two parts of a device interact or interface. An example of an electronically generated auditory stimulus is a beeper or a speaker that plays spoken instructions. An audio output as disclosed herein includes but is not limited to music, a sound, a beep, a series of beeps music or sounds, a mechanical sound including clicking, a sound replication of operation or behavior of a nasal drug delivery device containing medicament. These auditory stimuli, such as two parts of a device interlocking or interfacing can be picked up by a microphone of the system. The system can then identify whether or not the device was used correctly (i.e., whether a step was performed correctly or in the correct order, for example). A combination of both visual and auditory output may include a video tutorial providing instructions to a user on proper administration of the medicament or use of the training device, for example.

Somatic stimuli or feedback, also called somatosensory stimuli or tactile feedback, is typically generated mechanically. In a typical embodiment of the training device, there are a large number of somatic stimuli such as actuation forces, abrasion resistance, frictional forces, spring compression, the feel of a click if two parts interlocking, surface texture, vibrations, weight sensation, and any other similar stimuli or feedback known to those of skill in the art. These somatic stimuli or feedback may be replicated in the training device to simulate the nasal drug delivery device.

Figure 1B:
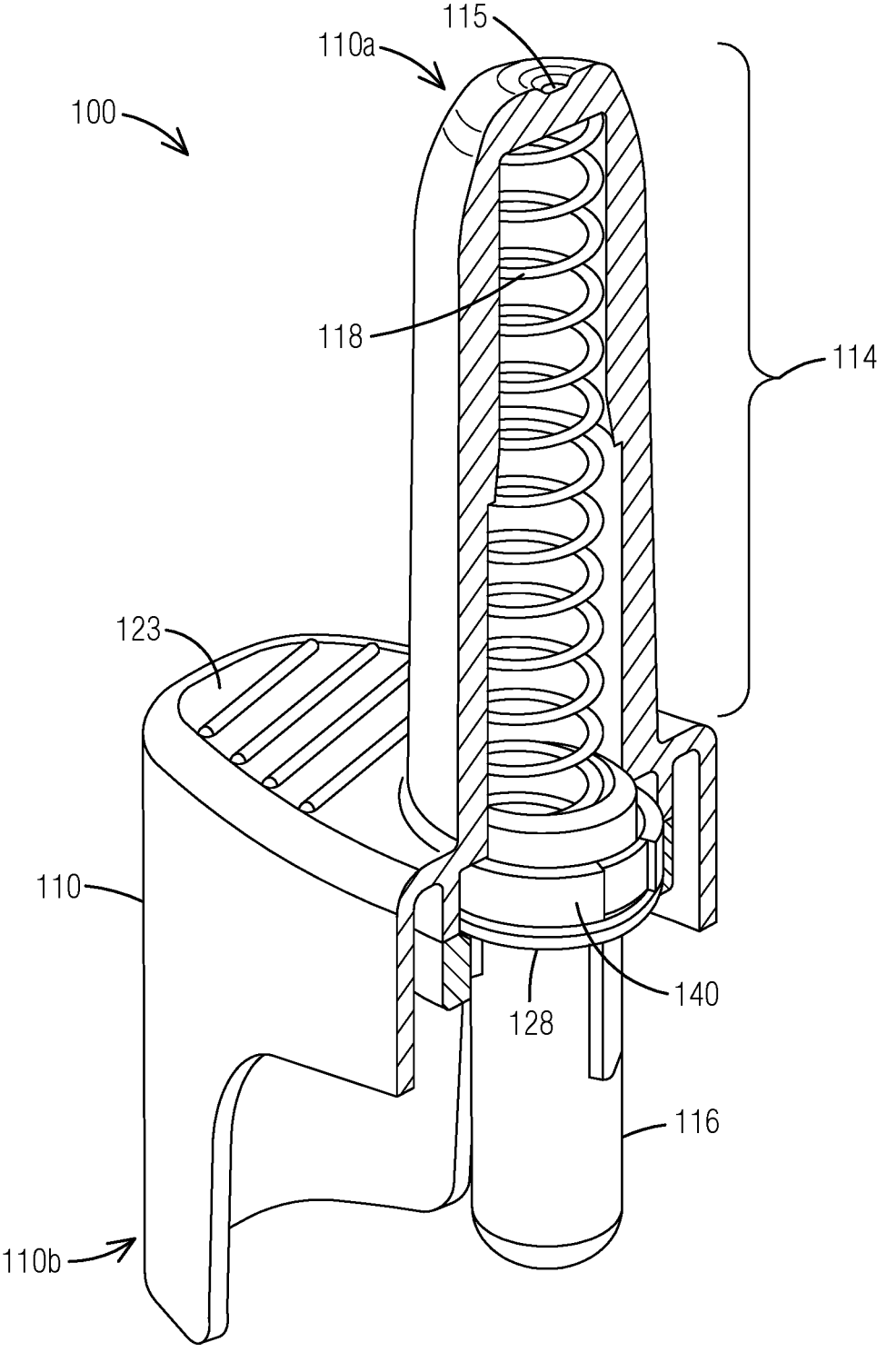
FIG. 1B is a partial perspective view of an embodiment of a nasal drug delivery training device.

Turning to the Figures, FIGS. 1A-1B are cross sectional views of an embodiment of a nasal drug delivery training device 100 including a housing 110 having a proximal end 110*a* and a distal end 110*b*. The housing 110 further includes a nasal interfacing portion 115, and a protrusion 114 including the nasal interfacing portion 115, in some embodiments. The protrusion 114 may be provided to be receivable within a nostril of a user. Consequently, the protrusion 114 is of a shape and size to abut, contact and/or traverse the nasal opening, in varying embodiments, and, in some examples, at least partially enter the nasal cavity. In a nasal drug delivery device, the drug may need to be delivered into a nasal cavity, and consequently, a protrusion 114 of the device as shown in FIGS provided herein may extend to the upper portion of the nasal cavity, in some embodiments, to effectively deliver and disperse the drug. The training device 100 may simulate the structural features of a drug delivery device in as much as the protrusion 114 may be of a size and shape that would be required to deliver drug through the nasal cavity.

In some embodiments described herein, the housing 110 may include a cavity 112. A plunger 116 is receivable within the cavity and moves proximally and distally relative to the device 100. The plunger 116 is therefore movable relative to the housing 110 and moves between a retracted position, and an extended position. In FIG. 1, the plunger is shown in its extended position 116. The device 100 further includes a plunger biasing member 118 associated with the plunger 116, biasing the plunger 116 in the extended position as shown in FIG. 1. The device embodiment 100 shown in FIG. 1 further includes a shoulder portion 123, wherein in one embodiment the housing 110 forms the shoulder portion 123. The shoulder portion 123 is provided to assist a user in gripping the device 110. The device further includes a locking member 120 for releasably locking the plunger 116 in a retracted position post use until the device 100 is reset. The plunger 116 is in a retracted position when the biasing member 118 is in a biased, or energized position. The biasing member 118 is shown in a released position when the plunger 116 is in the extended position in FIGS. 1A-1B.

In a nasal drug delivery device, the plunger drives delivery of medicament. In the nasal drug delivery training device embodiments herein, drug delivery is simulated when the plunger 116 is moved toward the proximal end of the device 110 to its retracted position, in some embodiments, against the resistance of a biasing member 118. The plunger 116 may further include a flange 140 near its proximal end and a locking member interfacing portion 116. In one embodiment the locking member interfacing portion may include a rail portion 124. The locking member 120 of the nasal drug delivery training device 100 may include a plunger interfacing portion, for example, a locking member tab 126. Actuation of the plunger 116 by moving the plunger toward the proximal end 110*a* of the housing 110, in one embodiment, causes the locking member interfacing portion 124 to interface with the plunger interfacing portion 126 (plunger interfacing portion not shown in cross-sectional view of FIGS. 1A-1B) of the locking member 120. In some non-limiting embodiments, this interface may cause the locking member 120 to rotate such that the plunger interfacing portion (locking tab 126) rotates away from the rail portion 124, allowing the rail portion 124 to pass through the locking member 120 as the plunger 116 moves into a retracted position. In some non-limiting embodiments, the locking member 120 is rotatable relative to the housing 110.

In some non-limiting embodiments, the plunger 116 may be rotatable relative to the housing 110. Upon movement of the plunger 116 relative to the locking member 120, the plunger 116 traverses the locking member and advance to its retracted position. Upon reaching the retracted position, the locking member 120 may rotate (or the plunger 116 may rotate, or both), such that the locking member 120 interfaces with a portion of the plunger 116 to lock the plunger 116 in a retracted position until the device 100 is reset for a subsequent use.

The locking member 120 may rest in a retainer member 130 in the housing 110 as shown in FIGS. 1A-1B. The retainer member 130 may also include a locking member spring 128, in some embodiments, which may associate with the locking member 120 and cause the locking member 120 to rotate, for example. In some embodiments, the locking member spring 128 may include a torsion spring. The retainer member 130 may include a retainer member opening 132 to allow for the passage of the plunger 116 therethrough.

A plunger biasing member 118 may be energized when the plunger 116 is in a retracted position, in one example. In another non-limiting example, the plunger biasing member 118 may be energized when the plunger 116 is in an extended position. In some non-limiting embodiments, the plunger biasing member 118 may include a compression spring or a torsion spring. The plunger biasing member 118 may interface between a portion of the plunger 116 and a portion of the housing 110, namely the proximal end of the housing 110*a* as shown in FIG. 1, for example.

Figures 1C, 1D:
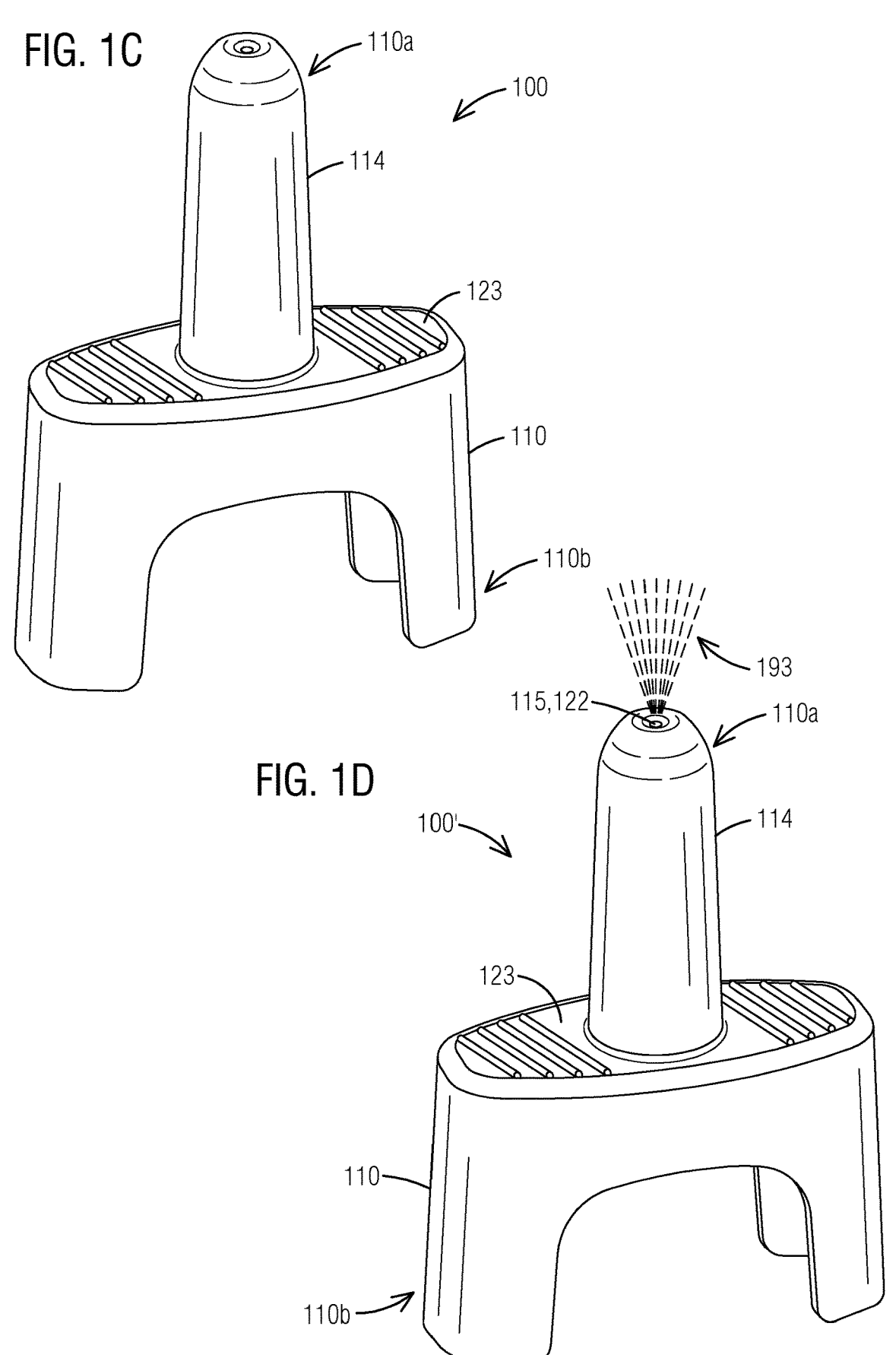
FIG. 1C is a perspective view of an embodiment of the nasal drug delivery training device shown in FIG. 1A-1B.
FIG. 1D is a perspective view of another embodiment of a nasal drug delivery training device including a fluid.

In some non-limiting embodiments, the nasal interfacing portion 115 may include an aperture 122 for delivering a fluid 193 to a user to simulate a drug delivery, as shown in the embodiment 100' of the nasal drug delivery training device of FIG. 1D. Therefore, in some embodiments the aperture 122 is configured to provide fluid flow into and out of the device 100. The fluid may include normal saline, pressurized air, sterile water, or other fluid for simulating drug delivery with the device 100'. Consequently, upon inserting at least a portion of the protrusion 114 into, or placing the protrusion adjacent to a nostril of a user, the plunger 116 is actuated, such that it is moved in a proximal direction, energizing the biasing member 118, actuating the device. In some embodiments wherein the device includes an aperture 122 on the nasal interfacing portion 115 as shown in FIG. 1D and a fluid 193 to be delivered therethrough. Actuation of the device 100' by activating the plunger 116 causes a fluid to be released into the nasal cavity of the user via the aperture 122 in the nasal interfacing portion 115 of the device. Other embodiments may not include an aperture 122, and may not include a fluid to be delivered from the device.

Figure 1E:
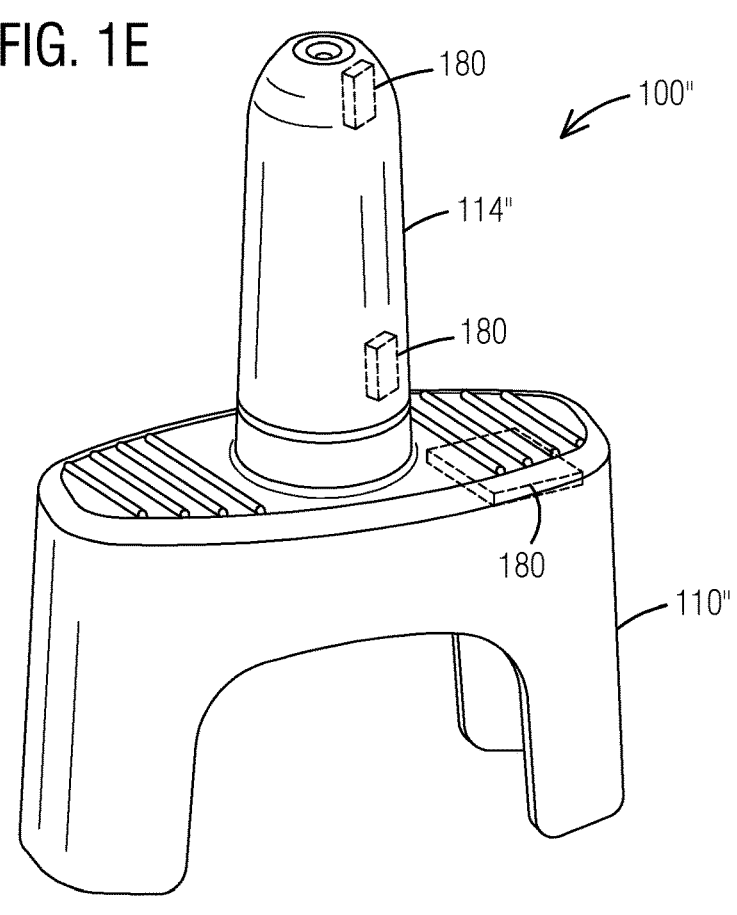
FIG. 1E is a perspective view of an embodiment of a nasal drug delivery device including sensors.
Figure 1F:
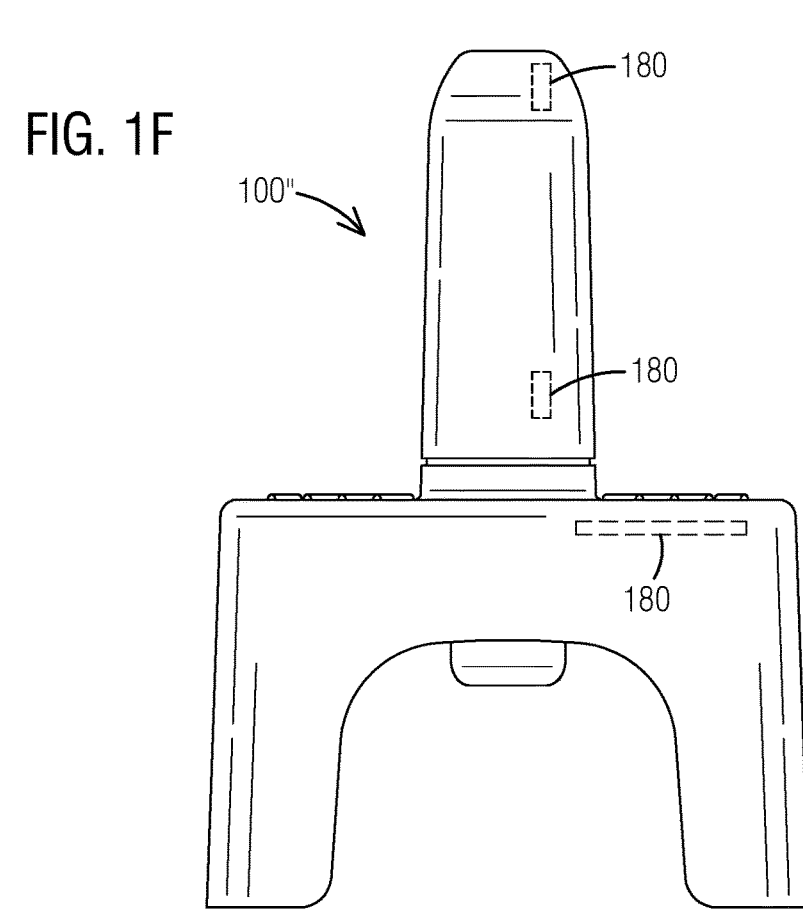
FIG. 1F is a side view of the device shown in FIG. 1E.

FIGS. 1E-1F provide an embodiment 100" of a nasal drug delivery training device, wherein one or more sensors 180 may be provided therein. The one or more sensors 180 may include any sensor described herein, or known to those skilled in the art to sense or detect a condition of the device. The sensors may include, in a non-limiting example, a fluid flow sensor or a flow rate sensor to detect the amount or rate of fluid passing through the device (for example in the device 100' of FIG. 1D). The sensors 180 may also, or alternatively include a contact sensor, a light sensor, a vibration or microphone or accelerometer, in other non-limiting embodiments. The particular locations of the sensors 180 shown in FIGS. 1D-1F are shown for example only, and the device embodiments described herein are not limited by the location of the sensors 180 shown in the FIGS.

Moreover, the devices are not limited to the number of sensors 180 shown in the FIGS herein, the FIGS display a number of sensors by way of example only. Embodiments of the devices may not include any sensors, or may include one or more sensors in various non-limiting examples.

Figure 2C:
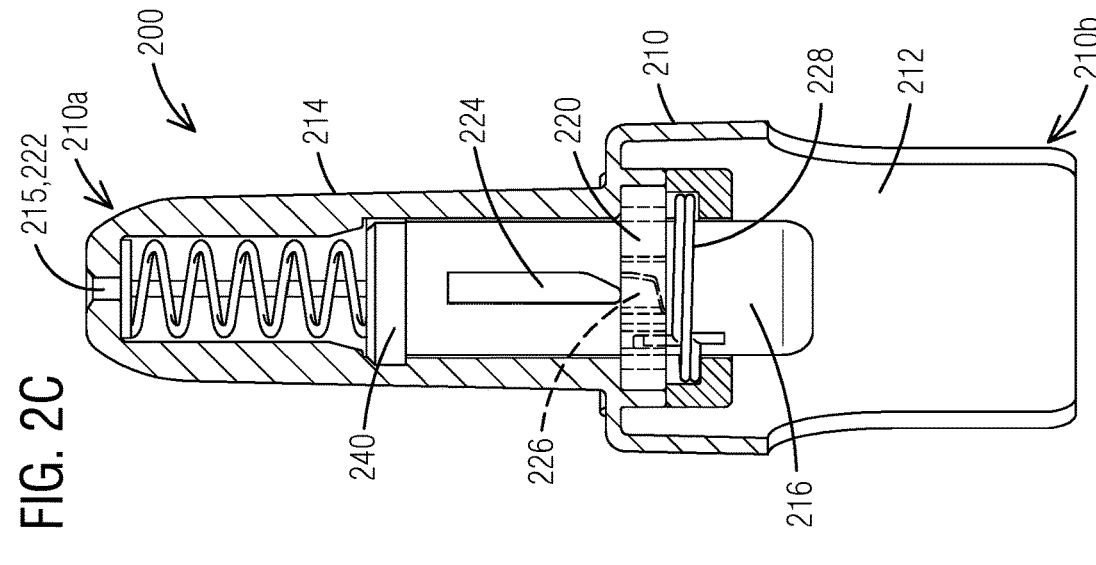
FIGS. 2A-2C are cross sectional views of another embodiment of a nasal drug delivery training device.
Figure 2B:
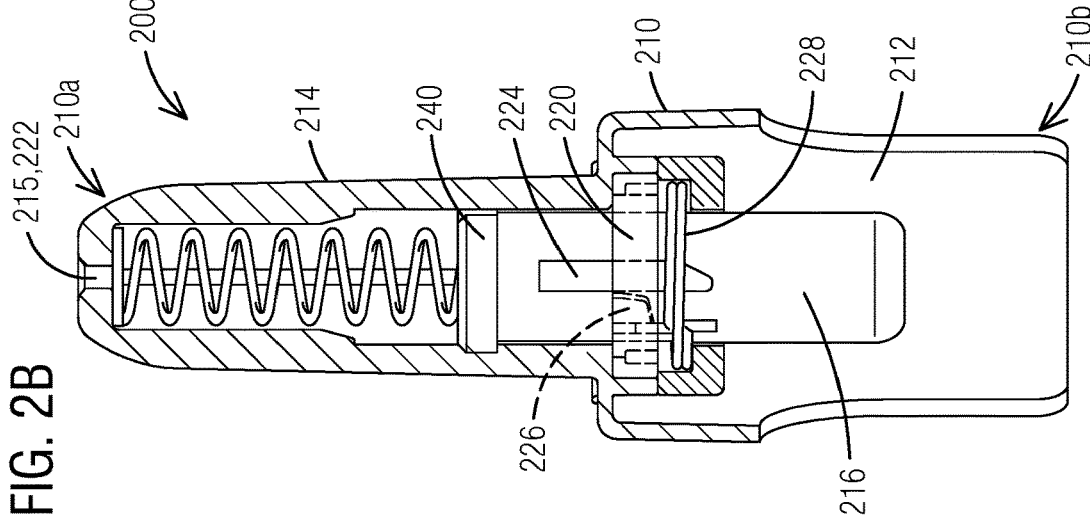
Figure 2A:
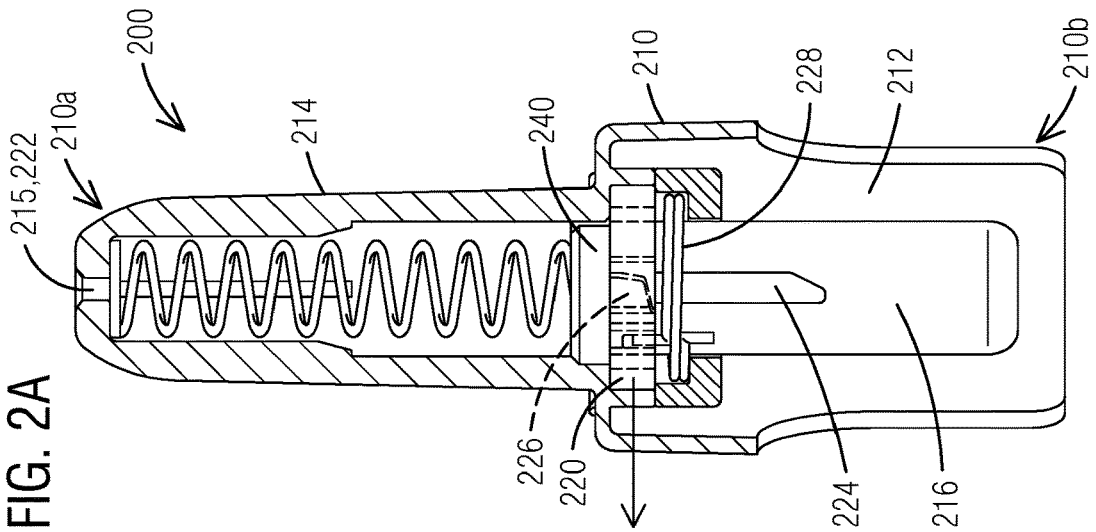

FIGS. 2A-2C are cross sectional views of another embodiment of a nasal drug delivery training device 200. The device 200 in FIG. 2A-2C includes a housing 210 having a proximal end 210*a* and a distal end 210*b*, the housing 210 defines a cavity 212. The device 200 further includes a nasal interfacing portion 215. In some non-limiting embodiments, the nasal interfacing portion 215 may include an aperture 222 for providing fluid communication between the user and the device 200. The nasal interfacing portion 115 includes a protrusion 214 as shown in FIG. 2A-2C, in one non-limiting embodiment, for interfacing with a nostril of a user.

The device 200 further includes a plunger 216 for moving between the proximal end 210*a* and the distal end 210*b* of the device 200. The plunger 216 may include a locking member interfacing portion 224, and a flange 240. The device 200 may further include a locking member 220 for interfacing with the plunger 216, in one embodiment. The locking member 220 may include a plunger interfacing portion 226. The plunger interfacing portion may be provided on the inner surface of the locking member 220. The plunger interfacing portion may be configured to interface with the locking member interfacing portion 224 during use of the device 200. In one example, the plunger interfacing portion may include a locking member tab 226, and the locking member interfacing portion may include a rail 224 on the plunger 216. During use of the device 200, the plunger interfacing portion 226 and the locking member interfacing portion 224 interface to allow selective extension (as shown in FIG. 2A) and retraction (as shown in FIG. 2C) of the plunger 216, and further to provide for locking the plunger 216 in a retracted position following use, and prior to reset, of the device.

As shown in FIG. 2A, the device 200 is in a ready-to-use position. The plunger flange 240 is positioned above the locking member 220 to maintain the plunger within the device. The plunger flange interfaces with the locking member 220 to maintain the plunger 216 in the pre-use, extended position, in one embodiment. Upon movement of the plunger 216 toward the proximal end of the device 210*a*, the plunger rail 224 interfaces with the locking member tab 226, rotating the rotating locking member 220 in a first direction. In an alternative embodiment, the plunger may rotate relative to the locking member 220 at this step, or the locking member 220 and the plunger 116 may rotate in opposing directions. This rotation allows the plunger 216 to pass through the locking member 220 to move toward the proximal end of the device 200, biasing the plunger biasing member 218 as shown in FIG. 2B. Further movement of the plunger 216 toward the proximal end upon application of a force on the end of the plunger 216 allows the rail 224 to pass through the locking member 220 by interaction between the rail 224 and the locking member tab 226 on an inner surface of the locking member 220, causing the locking member 220 to rotate, in one embodiment, in a first direction, and allow the plunger rail 224 to bypass the locking member 220. Once the plunger rail 224 bypasses the locking member 220, the locking member may rotate in a second direction, locking the plunger 216 in the retracted, locked position until reset of the device. In one embodiment, a locking member spring 228 rotates the locking member 220 in the second direction. In one example, the locking member spring 228 may include a torsion spring, which may be energized upon rotation of the locking member in the first direction, and released to rotate the locking member in the second direction. In one non-limiting embodiment, the first direction is opposite the second direction.

As shown in FIG. 2C, the plunger 216 is maintained in a retracted, locked position due to an interface between the plunger rail 224 and the locking member 220. In the embodiment shown in FIG. 2C the plunger biasing member 118 is not shown as fully compressed; however, in one embodiment, the plunger biasing member 118 may be fully compressed when the plunger 116 is in the retracted position. The embodiment 200 shown in FIGS. 2A-3C may represent a more compact embodiment of the device 200 or an embodiment representing an elongated housing 210 version of the device. This embodiment may be provided with or without a shoulder portion, wherein a small shoulder portion is shown in FIG. 2A-2C to assist in gripping the device during use. Moreover, in other non-limiting examples, the plunger 216 may include an extended portion, or may be associated with an elongated component configured to contact and actuate the plunger during use of the device. In one example a rod portion may extend from the plunger 216 and may be contacted by a finger of a user to actuate the device during use.

Figure 3:
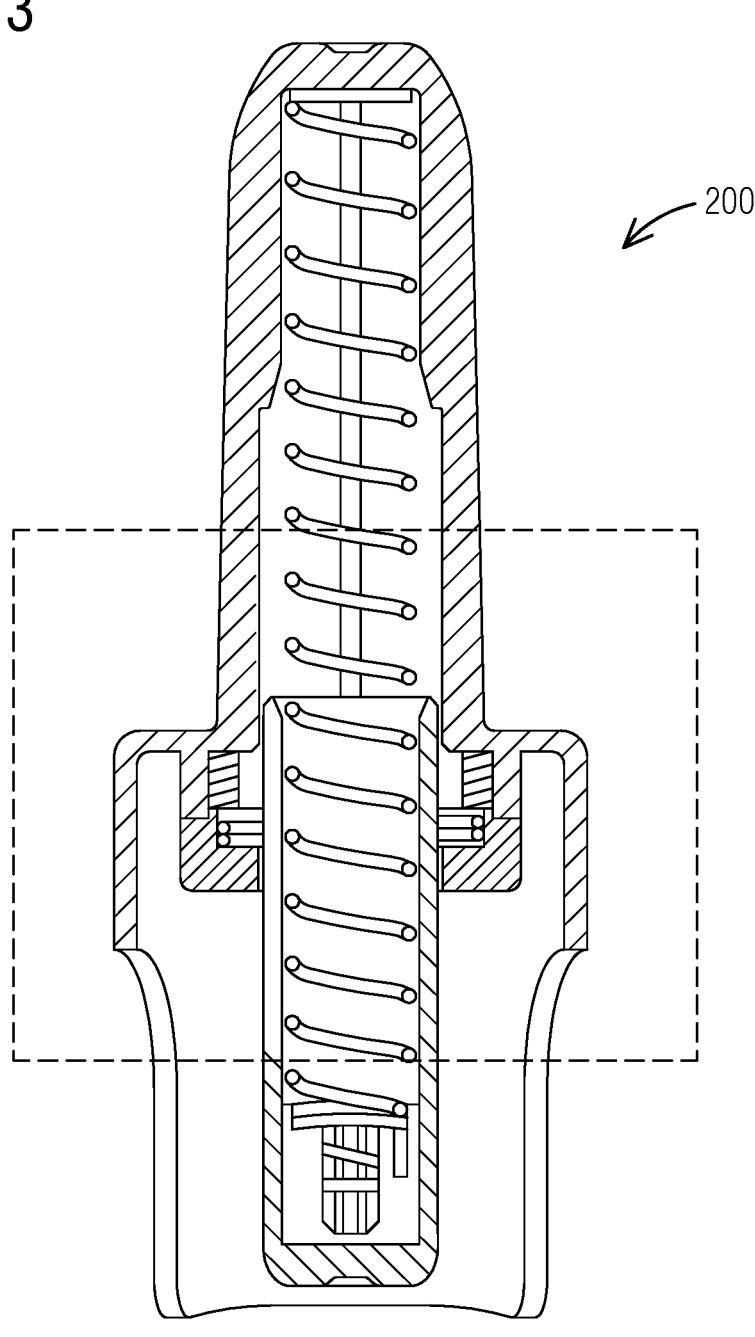
FIG. 3 is a cross sectional view of an embodiment of a nasal drug delivery training device.
Figure 4A:
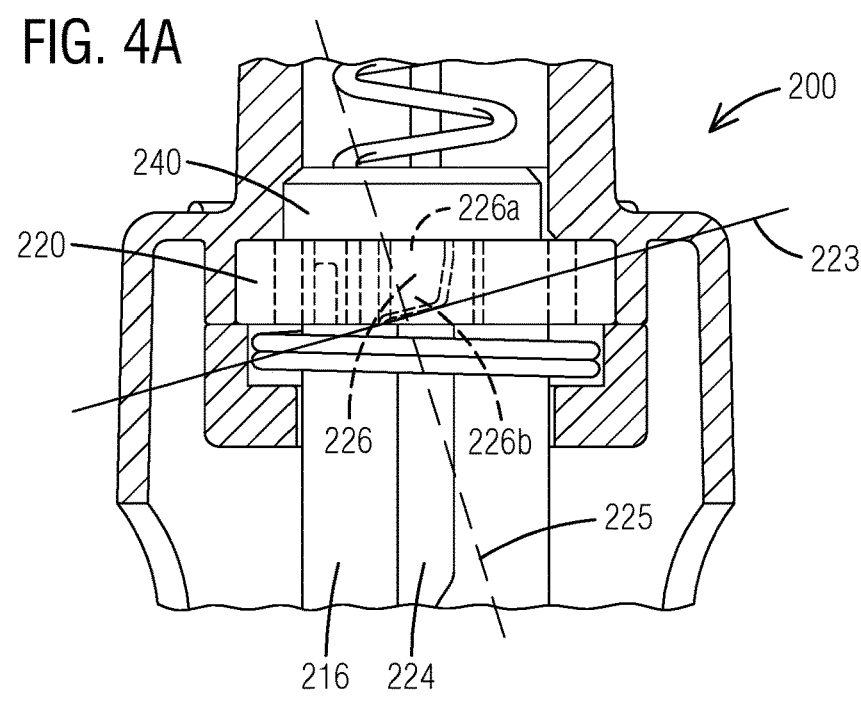
FIG. 4A is a partial cross sectional view of the nasal drug delivery training device embodiment shown in FIG. 3.
Figure 4B:
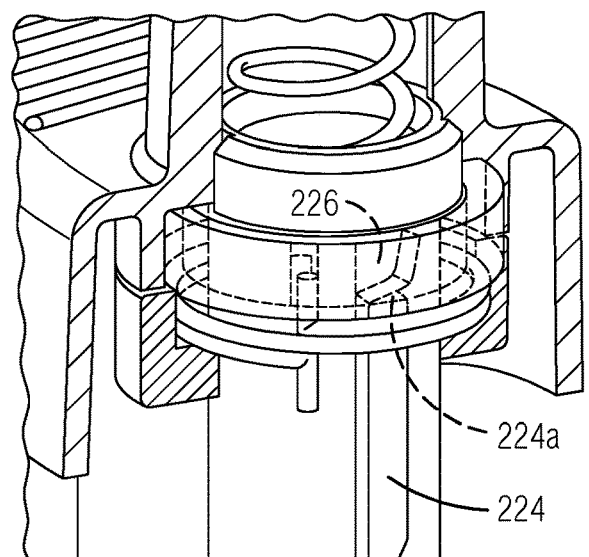
FIG. 4B is a partial sectional view of the embodiment of the nasal drug delivery training device shown in FIGS. 3 and 4A.

FIG. 3 is a cross sectional view of an embodiment of a nasal drug delivery training device 200. The selected region of FIG. 3 is shown in additional detail in the partial sectional views shown in FIGS. 4A-4B. FIGS. 4A-4B are partial sectional views of the nasal drug delivery device 200 portion outlined in FIG. 3.

Figure 4C:
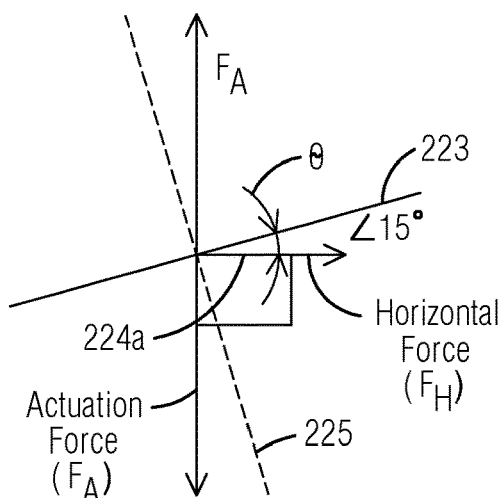
FIG. 4C is a graphical representation of the forces related to the training device shown in FIG. 4A, wherein the graph is superimposed on the device.

FIGS. 4A-4B shows the interactivity between the plunger flange 240, the locking member 220, and the plunger rail 224, in one embodiment. The locking member 220 includes a tab 226 on an inner surface thereof, as shown in dashed lines in FIG. 4A, for interfacing with the plunger rail 224 during operation of the device 200. The tab 226 includes a tab first surface 226*a* and a tab second surface 226*b*. During actuation of the training device 200, moving the plunger 216 toward the proximal end of the device to a retracted position, the plunger rail 224 interfaces with the locking member tab 226, in one example. Axial force is applied to the locking member tab 226 via the plunger rail 224 during plunger 216 movement toward the proximal end of the device. The tab second surface 226*b* may include an angled surface. In one embodiment, an angle θ is formed between the tab second surface 226*b* and a top surface of the plunger rail 224*a*. Angle θ may be between 10-20 degrees, in one non-limiting embodiment. This angle θ is also represented in the graph of FIG. 4C, wherein a ramp 223 formed by angled surface of the tab second surface 226*b* is shown, and the top portion of the plunger rail 224 is represented. Due to the angled surface of the tab second surface 226*b* and its interaction with the top surface of the plunger rail 224*a*, a break-out force occurs during movement of the plunger 216 relative to the locking member 220. The breakout force simulates a force of a nasal drug delivery device during actuation. Due to the interaction of the surfaces discussed herein, a reactive force 225 is created during movement of the plunger 216 in a proximal direction against the tab 226. This reactive force 225 is perpendicular to the ramp 223 as represented in FIG. 4C. Due to the perpendicularity of the reactive force 225 relative to the ramp 223 created by the angled surface of the tab second surface 226*b*, the horizontal force is less than the actuation force, causing a breakout force during actuation of the device 200 which occurs during movement of the plunger 216 against the locking member 220 toward the proximal end of the device 200. The break-out force simulates the force required to actuate a nasal drug delivery device and deliver an effective dose of medicament to a user.

Figure 5A:
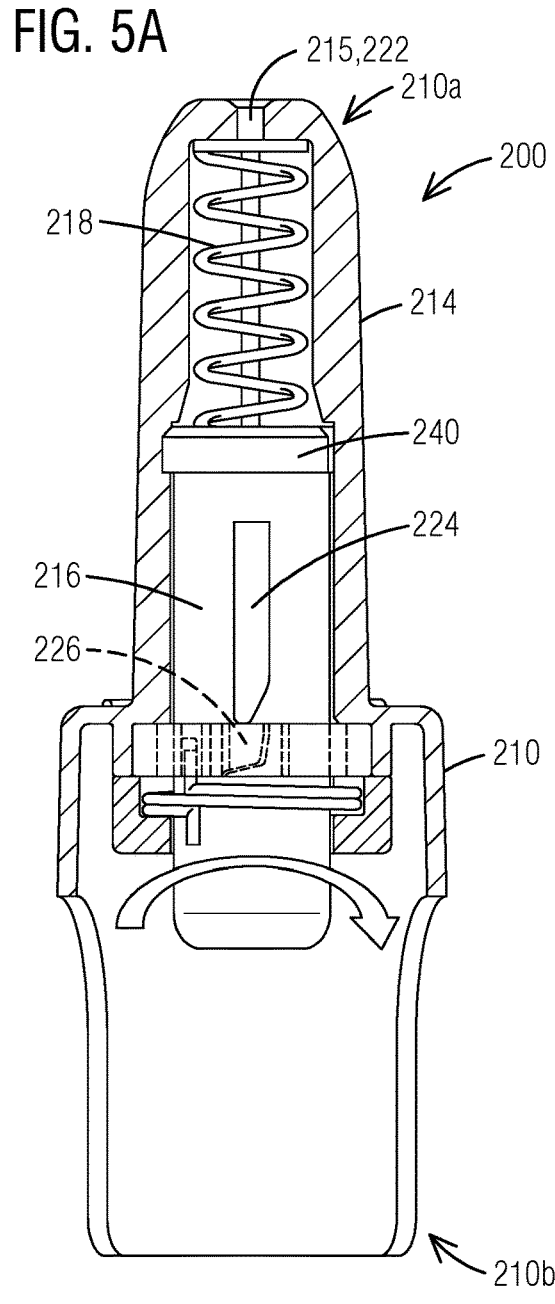
FIG. 5A-5D show partial cross sectional views of an embodiment of a nasal drug delivery training device demonstrating the various steps of reset.
Figure 5B:
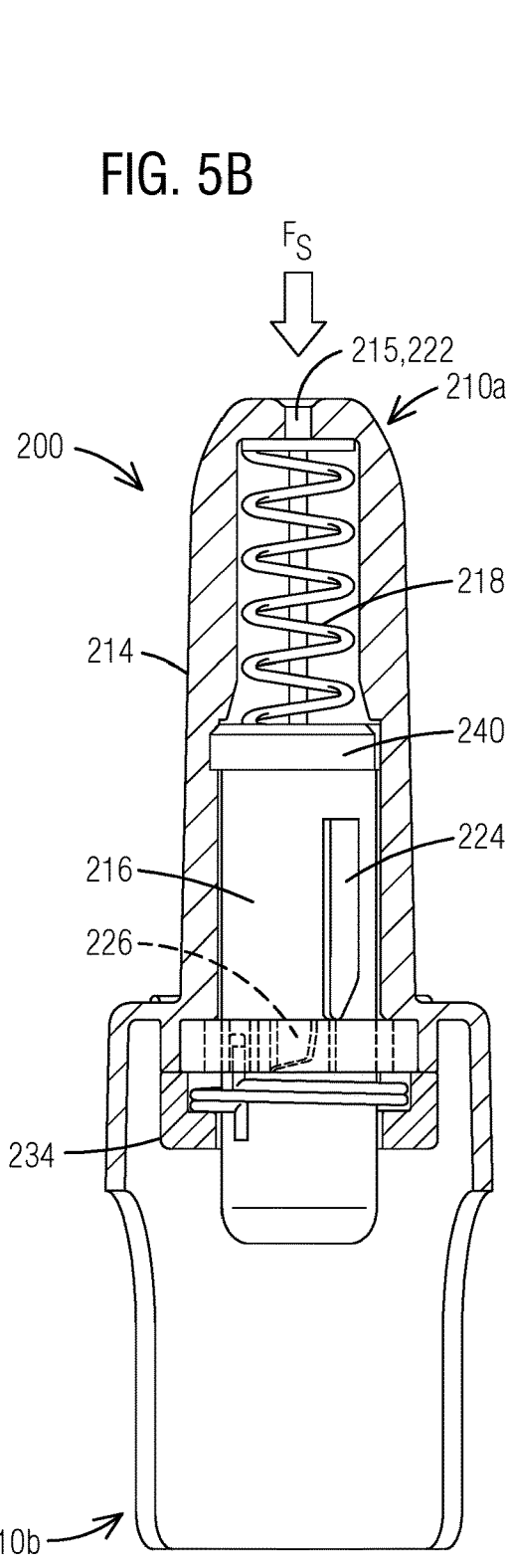
Figures 5C, 5D, 6:
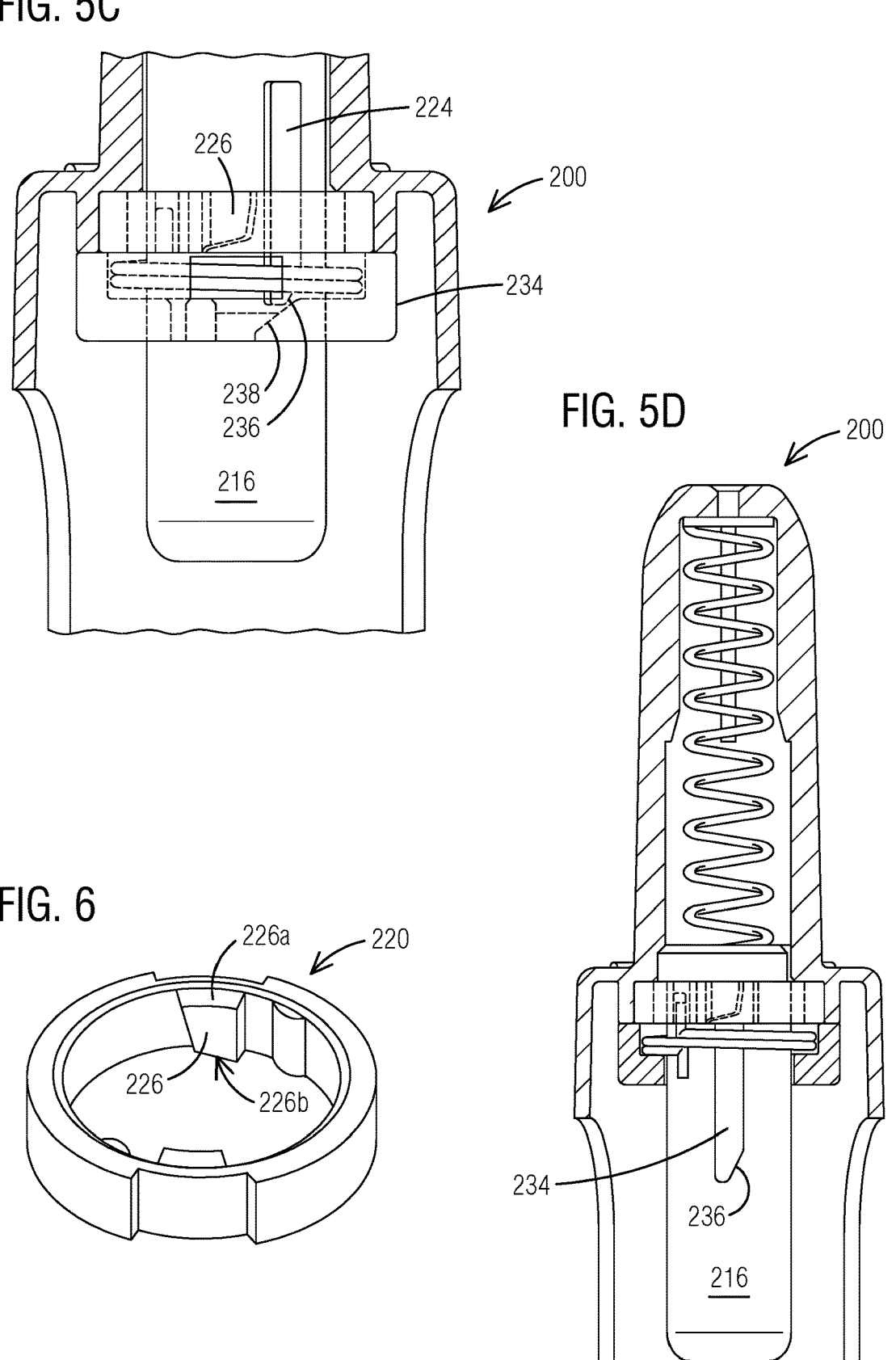
FIG. 6 is a perspective view of a locking member embodiment.

FIG. 5A-5D show partial cross-sectional views of an embodiment of a nasal drug delivery training device 200 during reset. In one embodiment, the plunger 216 is rotated in a first direction as shown in FIG. 5A until the plunger rail 224 is no longer in contact with the locking member tab 226 as shown in FIG. 5B to initiate reset. Once the plunger rail 224 is freed from the locking member tab 226, the plunger 216 is moved toward the distal end of the device as shown in FIG. 5C, toward an extended plunger position under the force of the plunger biasing member 218 in one non-limiting embodiment ($F_S$, spring force shown in FIG. 5B). As the plunger 216 moves toward the distal end of the device 210*b*, a retainer member ramp portion 238 of retainer member 234 interfaces with a ramp interfacing surface 236 of the plunger rail 224 as shown in FIG. 5D to position the plunger 216 in a pre-use, reset, extended position. Once the plunger 216 reaches this pre-use extended position, the device 200 has been reset and is ready for use for another training.

FIG. 6 is a perspective view of an embodiment of a locking member 220. The locking member 220 includes a locking member tab 226 having a first surface 226*a* and a tab second surface 226*b*, wherein the tab second surface 226 is an angled surface in one embodiment.

Figures 7A, 7B:
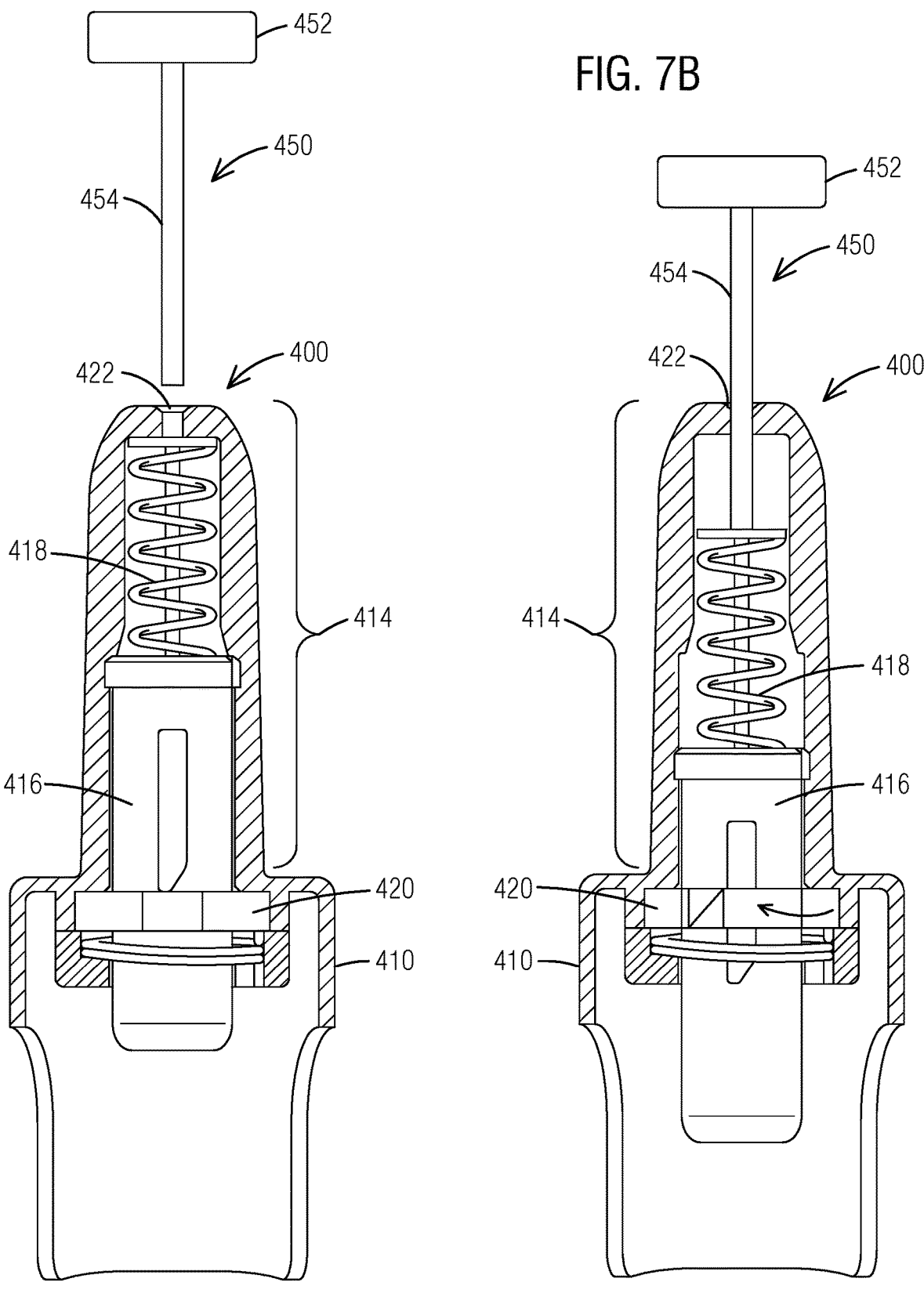
FIG. 7A is a cross-sectional view of an embodiment of a nasal drug delivery training device in a post-use position and an embodiment of a reset member.
FIG. 7B is a cross sectional view of the embodiment shown in FIG. 7A during reset.

FIG. 7A is a cross sectional view of an embodiment 400 of the nasal drug delivery training device in a retracted, post use position including a reset member 450. The reset member 450 includes a gripping portion 452 and an elongated portion 454 extending therefrom. The elongated portion 454 ends in a plunger interfacing tip 456, in one non-limiting embodiment. During reset of the device 400, the plunger interfacing tip 456 enters the aperture 422, and the elongated portion 454 extends into the protrusion 414 until the plunger interfacing tip 456 contacts the plunger 416. Movement of the reset member 450 further into the cavity of the device 400 in a distal direction, resets the plunger 416 an extended, pre-use position. In an alternative embodiment, the locking member 420 may be manually rotated in a first direction (or in a second direction) prior to insertion of the reset member 450 into the device 400 to prevent the locking member 420 from blocking the distal plunger 416 movement, providing a two-step reset. FIG. 7B is a cross sectional view of the embodiment 400 of the device and the reset member 450 shown in FIG. 7A. In FIG. 7B, reset of the device 400 by the reset member 450 is in process.

Figures 8A, 8B:
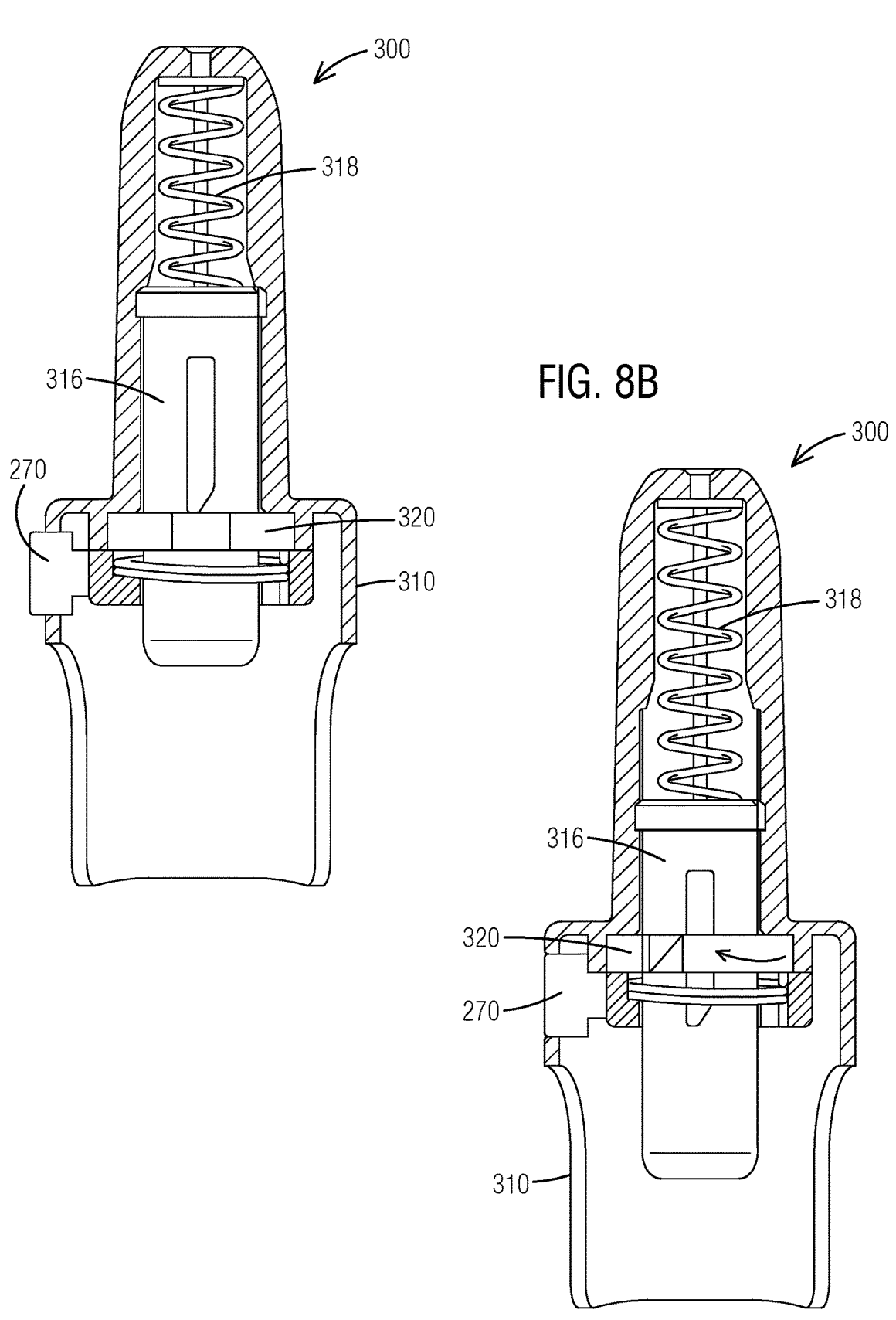
FIG. 8A is a cross sectional view of an embodiment of a nasal drug delivery training device in a post-use position, including an embodiment of a reset button.
FIG. 8B is a cross sectional view of the nasal drug delivery training device embodiment shown in FIG. 8A during reset.

FIGS. 8A-8B include a nasal drug delivery training device embodiment 300 including a reset button 270 on a portion thereof. The device 300 in FIG. 8A is shown in a post-use position, wherein the plunger is locked in a retracted position, and the plunger biasing member 318 is energized. Initiation of reset may occur by activating the reset button 270, such that the locking member 320 is displaced, and the plunger 316 is freed from the locking member 320. The plunger 316 may be either withdrawn from its retracted position manually or automatically extended upon actuation of the reset button 270. In one embodiment, the extension of the plunger 316 may occur by application of a force from the plunger biasing member 318 extending the plunger 316 to its reset, pre-use position, in one non-limiting embodiment. FIG. 8B shows a view of the nasal drug delivery training device 300 during reset.

FIGS. 9A-9E are examples of steps of a method of using a nasal drug delivery training device 100 according to one embodiment, including a protrusion 114 wherein the protrusion 114 is placed into, near, or in abutment with a nostril of a subject in a first step (FIGS. 9A-9B). In one embodiment, the device 100 must be positioned at 90 degrees. Following placement of the protrusion 114 into, in contact with, or adjacent to the nostril, the plunger 116 may be actuated as shown in FIG. 9C by moving the plunger into the housing 110 in a proximal direction to initiate the delivery of medicament (or to simulate delivery of medicament). In one non-limiting embodiment, a required activation force must be reached in order to simulate an effective dose delivery. Upon full retraction of the plunger 116, a shown in FIG. 9D the plunger 116 is locked in the retracted position as shown in FIG. 9D until the device 100 is reset for a subsequent use. In a further step shown in FIG. 9E, the device 100 may be unlocked and reset by rotating the plunger 116 in a first direction. Following rotation of the plunger 116, the plunger 116 extends to a pre-use position, either by force of the plunger biasing member, or by way of manually extending the plunger 116. Following extension of the plunger 116, the device 100 is reset for a subsequent training.

In alternative embodiments, reset may occur by rotation of or linear downward force on the protrusion. In yet other embodiments, reset may occur by way of actuation of a reset button 270 associated with the device 300 as shown in FIGS. 8A-8B. In at least one embodiment, the device may include a cover for placement over the protrusion so as to protect the protrusion and maintain sterility prior to use, or protect the user from contacting a protrusion of a device following insertion into, or placement of the protrusion in contact with or adjacent to the nostril or nasal cavity of a user.

Figure 10A:
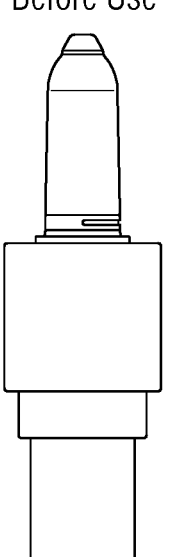
FIGS. 10A-10G include examples of steps of a method of actuating and resetting an embodiment of a nasal drug delivery training device.
Figure 10B:
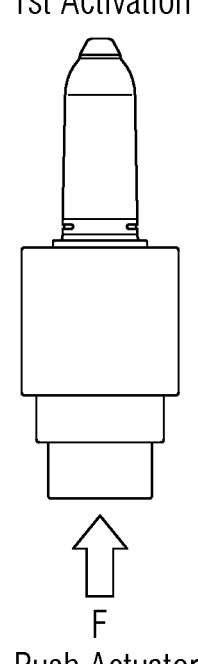
Figure 10C:
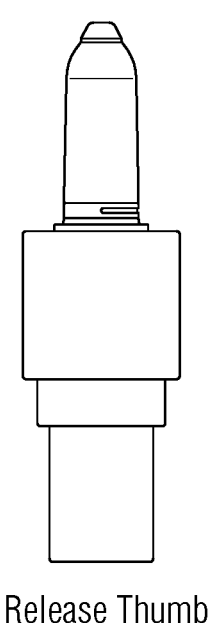
Figure 10D:
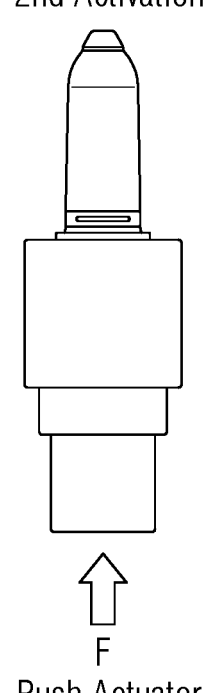
Figure 10E:
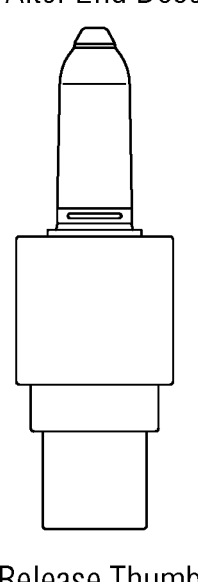

FIGS. 10A-10G provide an example of sequential steps of a method for using (actuating) and resetting an embodiment 500 of a nasal drug delivery training device. In one example, the embodiment 200 is configured for multiple actuations, i.e., to simulate multiple doses or actuations of a drug delivery device. In the particular non-limiting examples shown in FIGS. 10-17, the device embodiment 500 is configured for simulating a two-dose, two-actuation drug delivery device 500. FIGS. 10A-10E demonstrate the steps of activation of the device 500, from pre-use position to post-first actuation, wherein a first force is made to move the actuator 504 toward the distal end of the device 500 until the device 500 reaches a post-first actuation position shown in FIG. 10B completing simulation of a first actuation or a delivery of a first dose of medicament, for example. FIG. 10C shows the distal position of the actuator 504 once the force on the actuator 504 is released following first actuation. A second actuation occurs in FIG. 10D, wherein a second force to the actuator 504 moves the actuator toward the proximal end of the device 500 to cause a second actuation (the device reaches a post-second actuation position in FIG. 10E). The second actuation simulates a second dose, or a second actuation of a drug delivery device. Upon release of the second force on the actuator 504, after the second actuation, the actuator is maintained in the same position as during the second actuation as shown in FIG. 10D until reset of the device 500.

Figure 10F:
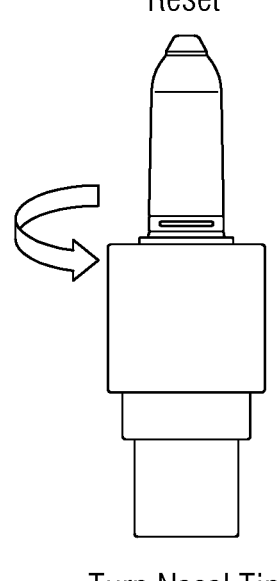
Figure 10G:
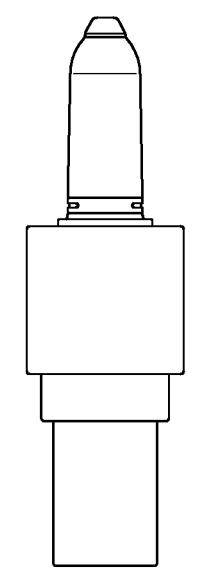

FIGS. 10F-10G demonstrate the steps to reset an embodiment 500 of the device. Reset is initiated by rotating the nasal interfacing portion of the device in a first direction, which resets the actuator 504 to a distal, pre-use position as shown in FIG. 10G, and resets the plunger to a pre-use position. This reset of the device serves to reset the internal components of the device back to their pre-use position, in preparation for a subsequent training with the device.

Figure 11:
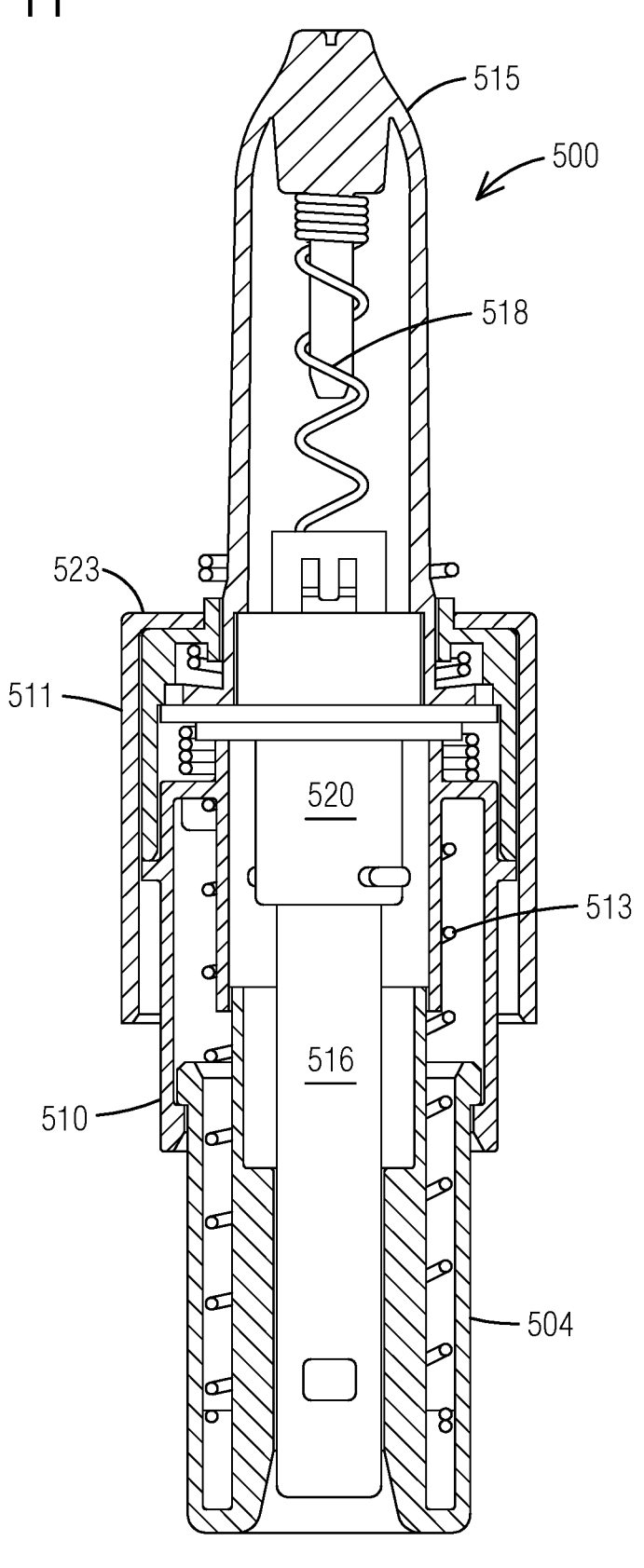
FIG. 11 is a partial sectional view of an embodiment of a nasal drug delivery training device.

FIG. 11 is a partial sectional view of an embodiment 500 of a nasal drug delivery training device. The device 500 includes a nasal interfacing portion 515, a housing 510, an optional shoulder portion 523, which may be formed by the housing 510 or by a removable finger flange 511 as shown in FIG. 11. The removable finger flange 511 and/or the shoulder portion 523 facilitate gripping and manipulating the device 500 during use.

Figures 12A, 12B:
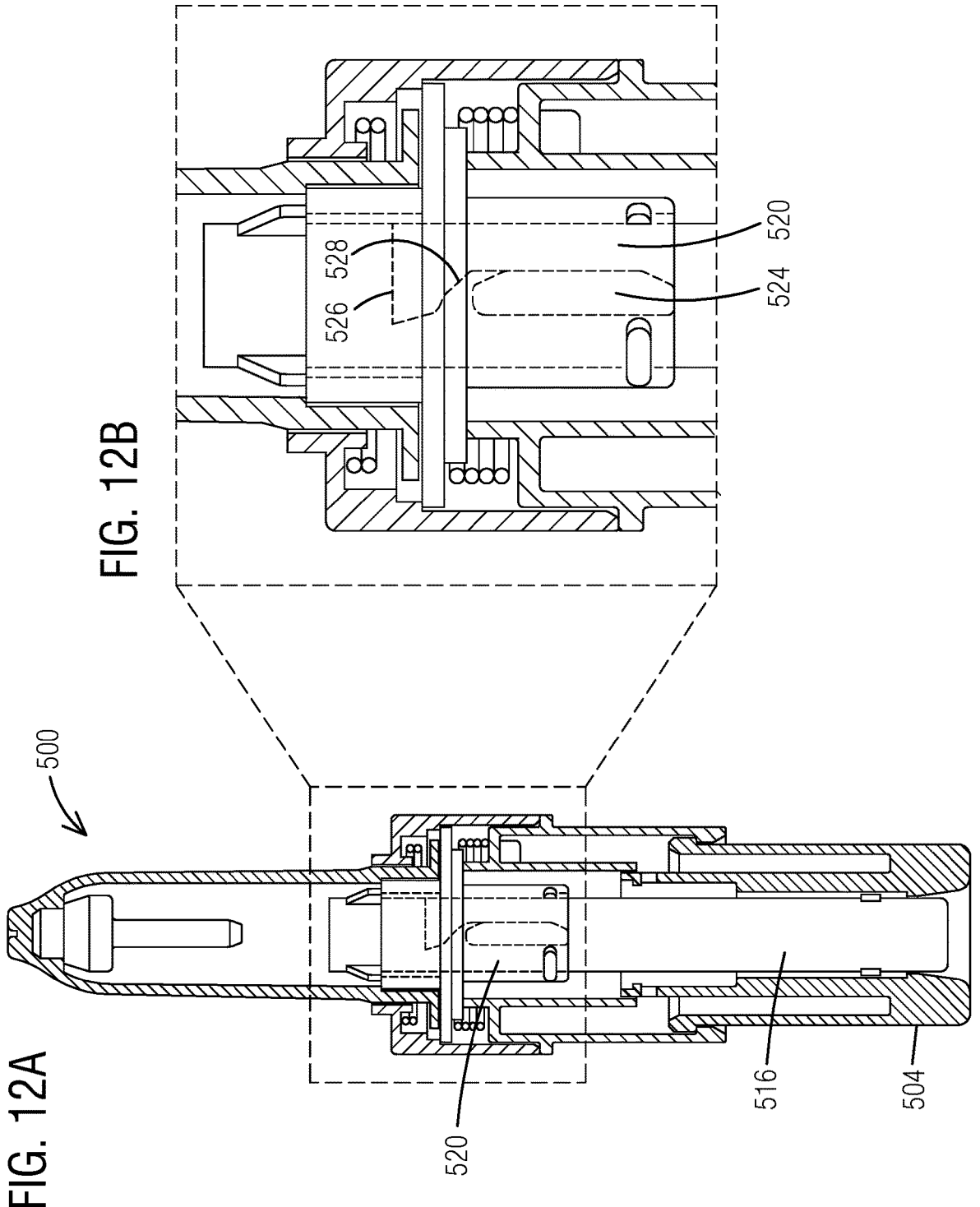
FIG. 12A is a partial cutaway side view of the embodiment of the nasal drug delivery training device shown in FIG. 11 prior to actuation.
FIG. 12B is a partial focused view of a portion of the nasal drug delivery training device shown in FIG. 12A.

FIG. 12A is a partial cutaway side view of the embodiment of the nasal drug delivery training device shown in FIG. 11 prior to actuation. Internal to the nasal interfacing portion may be provided a plunger biasing member 518 which biases the plunger 516 toward the distal end (toward its extended position) as shown in FIG. 11. An actuator 504 is shown, as well as an actuator biasing member 513, which biases the actuator toward the distal end of the device as shown in FIG. 11. A rotatable locking member 520 is shown in FIG. 11, wherein the locking member is rotatable relative to the housing. 510. Both the locking member 520 and the nasal interfacing portion 515 may rotate together by manipulation of the nasal interfacing portion during reset of the device 500 which is further explained in detail herein, particularly in reference to FIGS. 15-16.

Figures 12C, 12D:
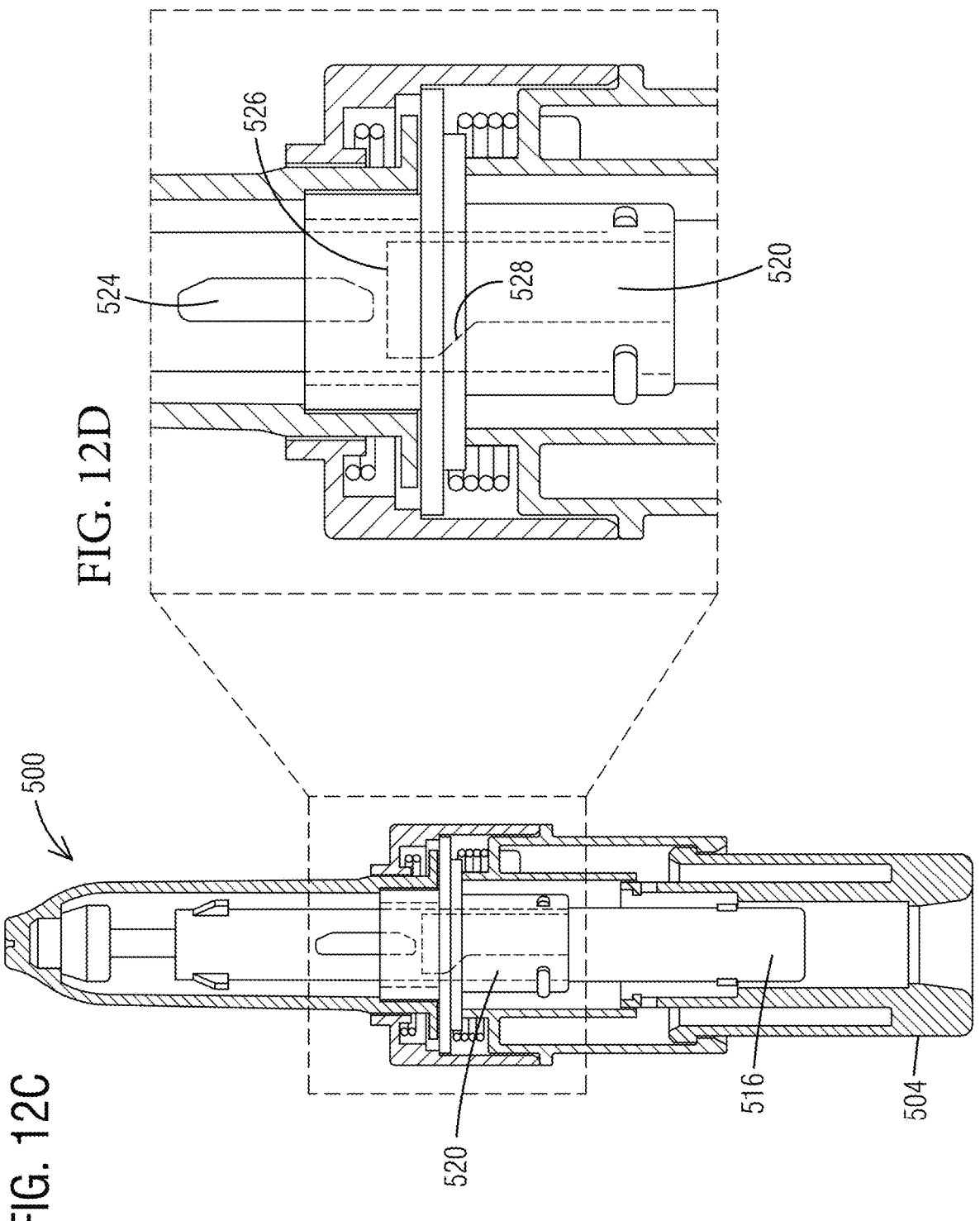
FIG. 12C is a partial cutaway side view of the embodiment of the nasal drug delivery training device shown in FIG. 12A-12B following a first actuation.
FIG. 12D is a partial focused view of a portion of the nasal drug delivery training device shown in FIG. 12C.

FIG. 12B is a partial focused view of a portion of the nasal drug delivery training device shown in FIG. 12A demonstrating the interaction between the plunger tab 524 and the locking member ramp 528 during the first actuation. This interface between the plunger tab 524 and the angled locking member ramp 528 causes rotation of the locking member 520 in a first direction as the plunger 516 is retracted as shown in FIGS. 12A-12D until the plunger tab 524 bypasses the ramp 528. As shown in FIG. 12 herein, in at least one embodiment, the locking member ramp 528 includes a fixed angle for interfacing with the plunger tab 524 The interaction between the plunger tab 524 and locking member ramp 528 as the plunger is moved into the device during a first actuation simulates a breakout force that occurs during actuation of a drug delivery device. In at least one example, this simulation occurs by way of an interface between at least two internal components of the device, at least one component which includes a fixed angled ramp, the locking member ramp 528.

FIG. 12C is a partial cutaway side view of the embodiment of the nasal drug delivery training device 500 shown in FIG. 12A-12B following a first actuation, wherein the plunger tab 524 has surpassed the locking member ramp 528. As shown in FIGS. 12C-12D, the locking member 520 has rotated back in a second direction once the plunger tab 524 bypassed the ramp 528. This rotation may occur by way of a locking member biasing member, which may in one example include a torsion spring. Once the plunger 516 and locking member 520 reach the positions shown in FIGS. 12C-12D, the post-first actuation position—the plunger tab 524 interfaces the locking member via its plunger locking surface 526 locking the plunger 516 in a retracted position, and preventing the plunger 516 from extending toward its distal end until the device 500 is reset. Once the actuator is pressed to retract the plunger 516 into the device 500 to complete the first actuation, the plunger 516 is maintained in its post-first actuation position as shown in FIG. 12C, but once the force on the actuator 504 is released, the actuator 504 extends to a pre-use position.

Figures 13A, 13B, 13C:
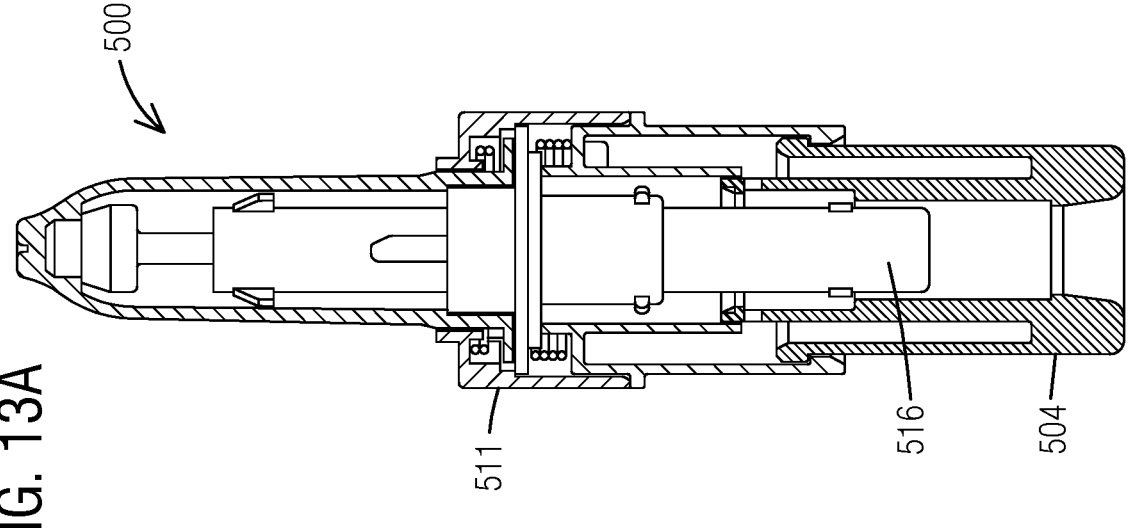
FIGS. 13A-C show sequential steps in a second actuation of the nasal drug delivery training device embodiment.
Figure 13D:
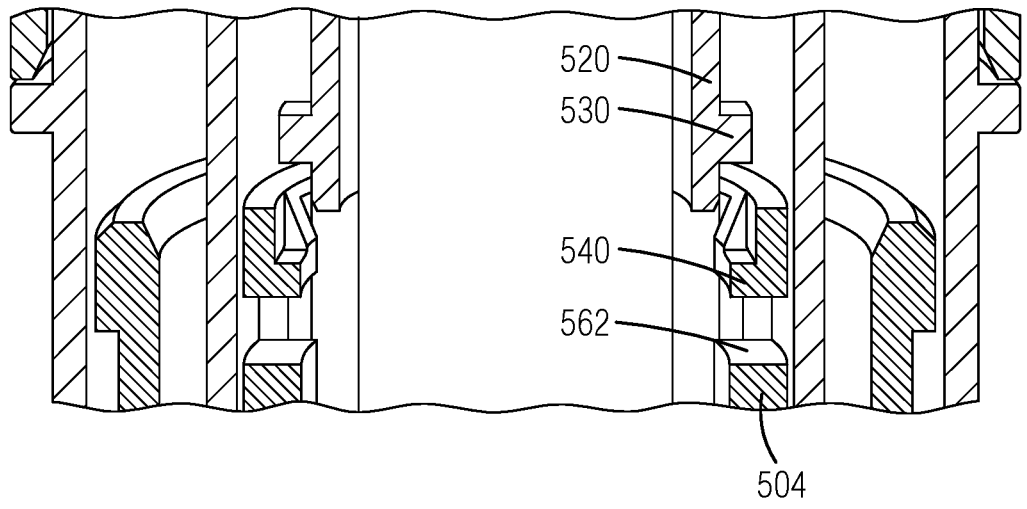
FIG. 13D is a partial sectional view of the device shown in FIG. 13B.
Figure 13E:
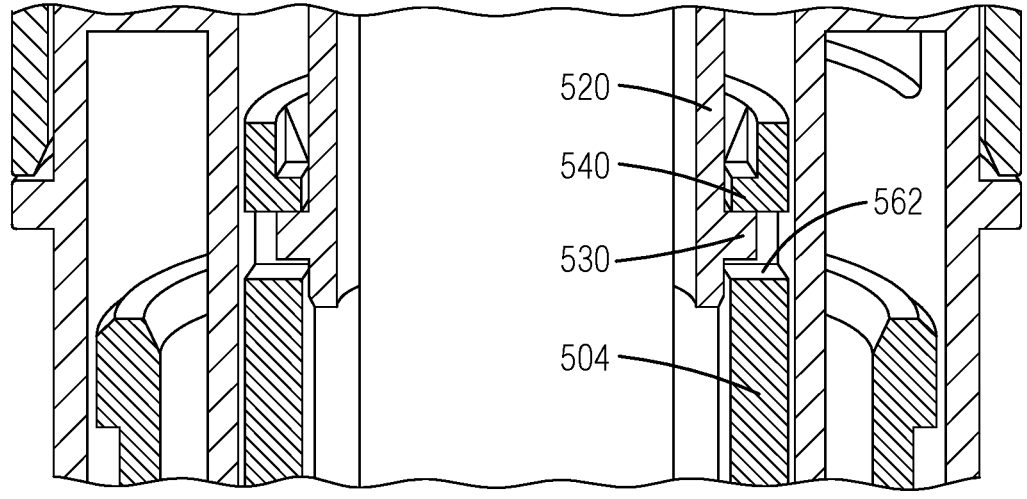
FIG. 13E is a partial sectional view of the device shown in FIG. 13C showing the snap fit feature.

FIGS. 13A-C show sequential steps of a second actuation of the nasal drug delivery training device 500, according to one embodiment, wherein a second force on the actuator 504 moves the actuator from an extended, distal position as shown in FIG. 13A to a retracted position as shown in FIG. 13*b*. Further movement toward the proximal end of the device as shown in FIG. 13B-FIG. 13C causes an actuator protrusion 540 to interface with the locking member tab 530, such that the locking member tab 530 is positioned within an actuator notch 562 as shown in FIG. 13E. This interaction may cause a snap fit between the actuator 504 and the locking member 520. The second actuation of the actuator 504 as shown in FIGS. 13A-13E causes a force that mimics a second breakout force. Once the device 500 reaches the post-second actuation position shown in FIG. 13E, the device 500 must be reset for a subsequent use.

FIGS. 14A-14E show the initial steps of reset of the device 500. To initiate reset, the nasal interfacing portion 515 is rotated in a first direction. By way of rotation of the nasal interfacing portion 515, the locking member 520 is also rotated. The relationship between these two components is shown in greater detail in FIGS. 15A-15B and 16A-16B. The initial rotation of the nasal interfacing portion and protrusion 515 initiates reset of the actuator 515. The rotation in the first direction removes the interface between the locking member tab 530 and the actuator protrusion 540. Once the locking member tab 530 is free of the actuator protrusion, the actuator 504 can extend proximally toward a reset position as shown in FIG. 14E. This extension may be powered by an actuator biasing member. The actuator biasing member may include a compression spring, in one non-limiting embodiment which causes the actuator 504 to extend as shown in FIG. 14E.

Figure 16A:
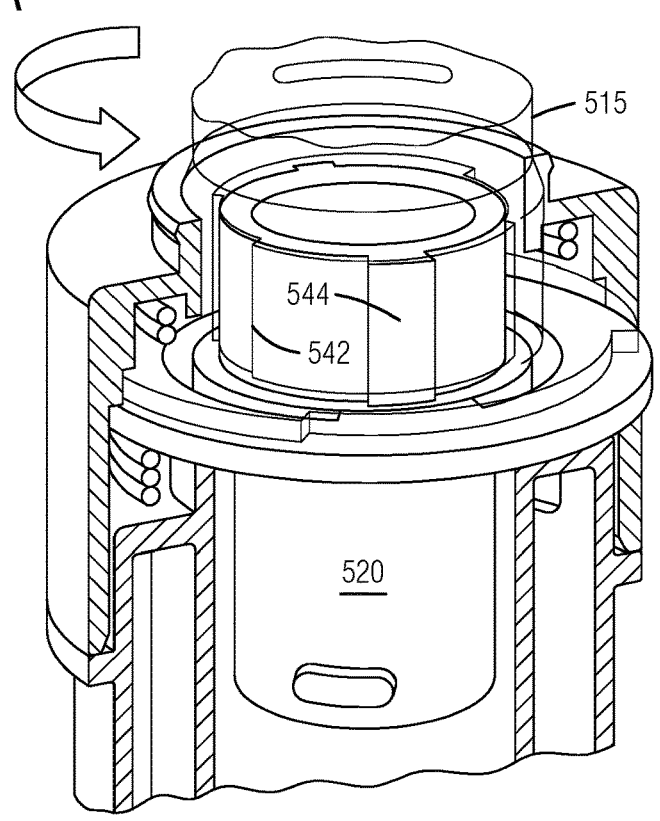
FIGS. 16A-16B show steps in rotation of the nasal interfacing portion, and rotation of the locking member.
Figure 16B:
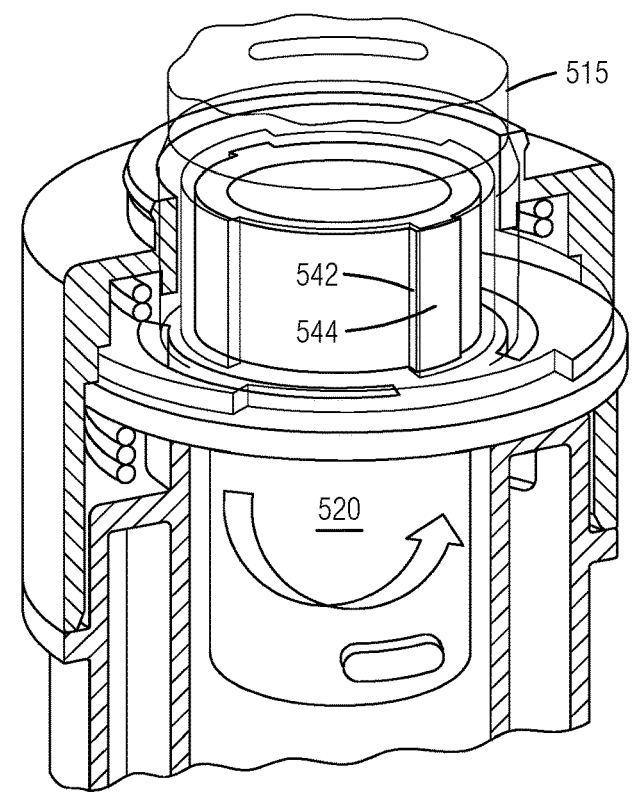

As described above, FIGS. 15A-15B show the interconnectivity between the nasal interfacing portion 515 via its nasal interfacing portion protrusion 542 shown in FIG. 15A and the locking member protrusion 544 of the locking member 520. FIG. 16A shows the nasal interfacing portion 515 and the locking member 520 within the device 500. FIG. 16B shows the interconnectivity between the nasal interfacing portion 515 and the locking member 520 via the nasal interfacing portion protrusion 542 and the locking member protrusion 544 upon rotation of the nasal interfacing portion 515.

Figures 17A, 17B, 17C:
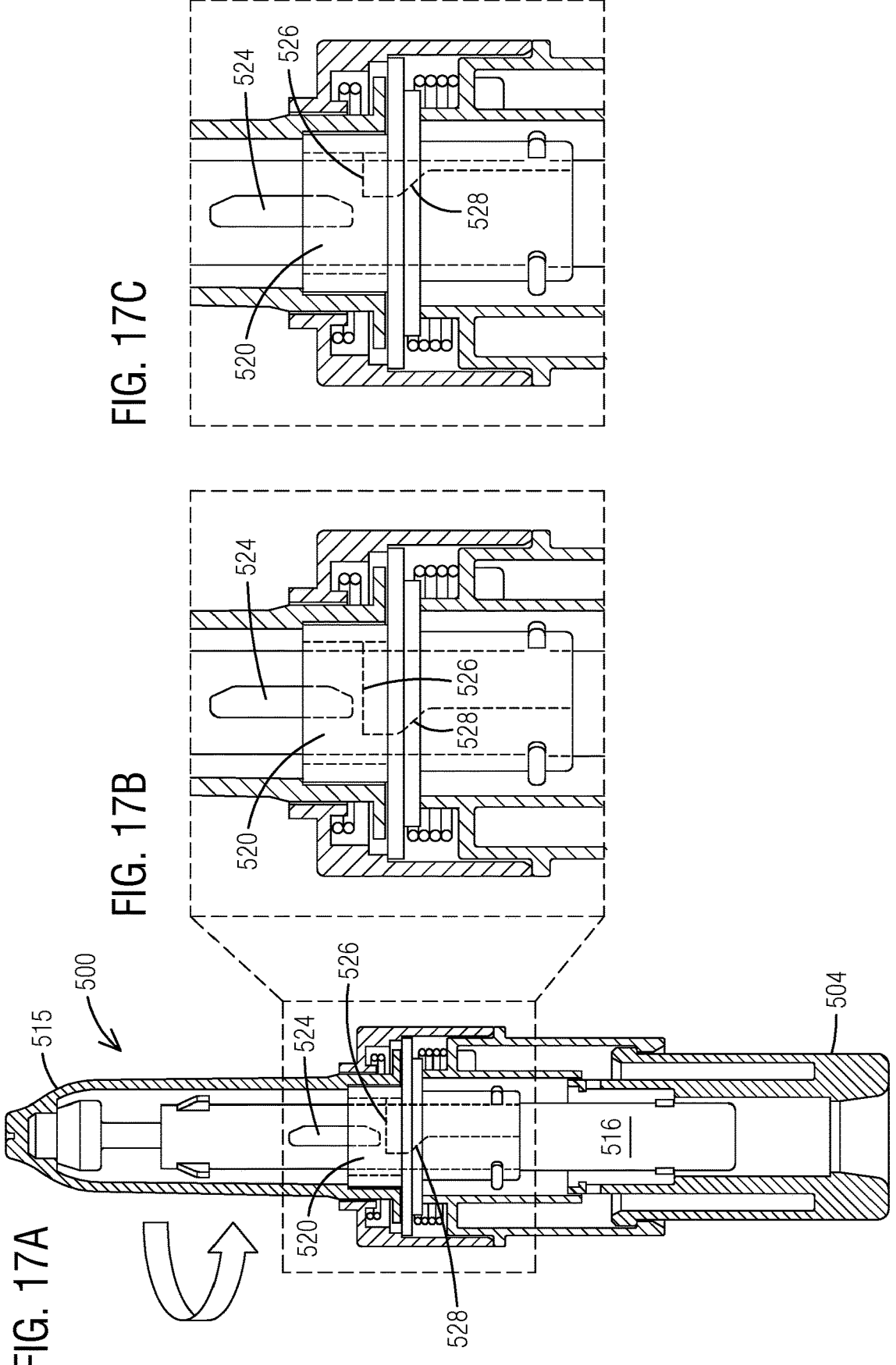
FIGS. 17A-17E show the remaining steps in the reset of the nasal drug delivery training device embodiment continuing from FIGS. 14A-14E.
Figures 17D, 17E:
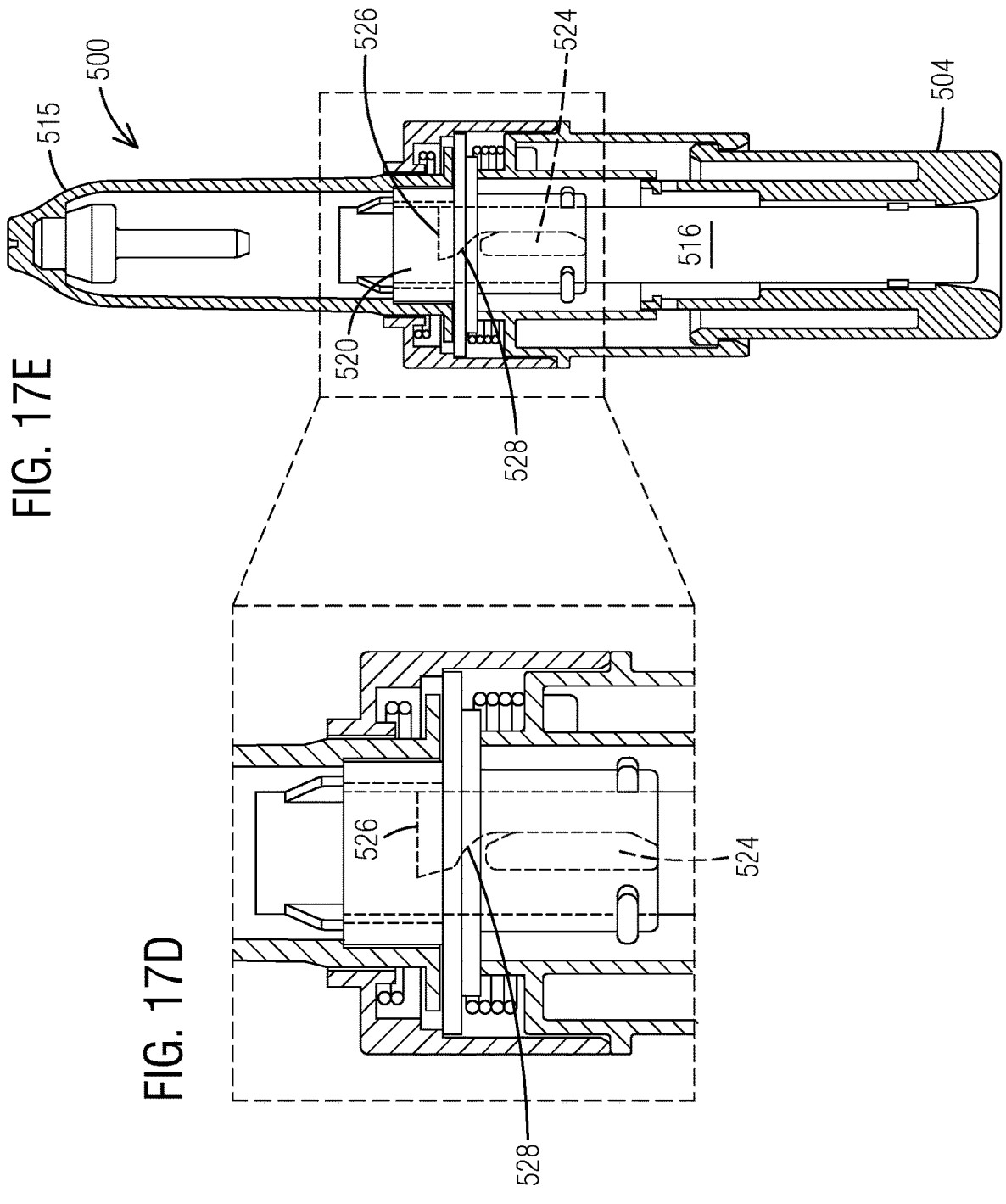

FIGS. 17A-17E show continued reset of the device 500, by further rotation of the nasal interfacing portion 515. . Once the actuator 504 is reset as shown in FIGS. 14A-E, continued rotation of the nasal interfacing portion 515 causes reset of the plunger 516. Further rotation of the nasal interfacing portion 515 in the first direction rotates the locking member 520 to remove the interface between the plunger tab 524 and the plunger locking surface 526 to unlock the plunger. Once the locking member plunger locking surface 526 is rotated out of the way of the plunger tab 524 as shown in FIG. 17C, the plunger 516 is able to fully reset as shown in FIGS. 17D-17E and extend back to its distal, pre-use position shown in FIG. 17E. The plunger biasing member 518 (shown in FIG. 11, but omitted in FIG. 17E) may cause the plunger 516 to fully extend to its pre-use position as shown in FIG. 17E. The device shown in FIG. 17E is fully reset for a subsequent use.

What is claimed is:

1. A nasal drug delivery training device for training a subject to deliver medicament to a nasal airway, the device having a pre-use position and a post-use position, the device comprising:

a housing comprising a cavity, a proximal end, and a distal end, and a nasal interfacing portion near the proximal end;

a plunger moveable relative to the housing, said plunger having a retracted position, and an extended position, said plunger comprising a plunger protrusion;

a plunger biasing member associated with the plunger for resetting the plunger to the extended position post use;

a locking member for locking the plunger in the retracted position following a simulation, the locking member rotatable in a first direction and a second direction, wherein the plunger protrusion is configured to interface with the locking member during actuation and reset of the device, and a torsion spring, wherein rotation of the locking member in the first direction energizes the torsion spring, and wherein the torsion spring causes rotation of the locking member in the second direction;

wherein movement of the plunger toward the proximal end of the housing simulates delivery of medicament to a nasal airway with a nasal drug delivery device, and wherein, optionally, (i) the nasal interfacing portion comprises a nasal protrusion for interfacing with a nostril of a subject, (ii) the nasal interfacing portion further comprises an aperture providing fluid communication between the cavity and a nostril of the subject, (iii) the biasing member biases the plunger toward the distal end of the housing, (iv) the housing further comprises a shoulder portion, (vi) the nasal interfacing portion is removable, and optionally, is replaceable and/or (vii) the protrusion is removable, and optionally, is replaceable.

2. The nasal drug delivery training device of claim 1, wherein, optionally, (i) the locking member interfaces with the plunger to lock the plunger in the retracted, locked position, (ii) the locking member is rotatable relative to the housing to selectively lock and unlock the plunger, (iii) the plunger is resettable from a locked, retracted position, to an unlocked position by unlocking the locking member, (iv) unlocking and/or reset of the device occurs by rotating a portion of the plunger, (v) the nasal interfacing portion is rotatable, and unlocking and/or reset of the device occurs by rotating the nasal interfacing portion and (vi) unlocking and/or reset of the device occurs by rotating a portion of the locking member.

3. The nasal drug delivery training device of claim 1, wherein the shoulder portion further comprises a gripping surface.

4. The nasal drug delivery training device of claim 1, wherein to simulate a drug delivery, during actuation of the device and retraction of the plunger to a first retracted position, the plunger protrusion interfaces with a ramped portion of the locking member, wherein movement of the plunger toward the retracted position causes the plunger protrusion to interface with the ramped portion, rotating the locking member in a first direction to allow the plunger to bypass the locking member as the plunger reaches its first retracted position, simulating a first breakout force of the device.

5. The nasal drug delivery training device of claim 4, wherein once the plunger protrusion bypasses the locking member, the locking member rotates in a second direction, and the plunger is maintained in the retracted position as the plunger protrusion interfaces with a plunger abutting ledge of the locking member.

6. The nasal drug delivery training device of claim 1, wherein the plunger is rotatable relative to the housing.

7. The nasal drug delivery training device of claim 1, wherein the locking member comprises a tab for interfacing with a rail, and optionally, (i) wherein the tab comprises a tab first surface for interfacing with the rail to lock the plunger in a retracted position, (ii) wherein the tab comprises a tab second surface for interfacing with the rail during movement of the plunger from an extended position to a retracted position, and (iii) wherein actuation of the plunger causes the rail to interface with the tab of the locking member, such that the locking member rotates in a first direction, or the plunger rotates in a second direction, or both, allowing the plunger to traverse the locking member and advance toward an extended position.

8. The nasal drug delivery training device of claim 7, wherein upon movement of the plunger to its retracted position, the rail traverses the locking member, and the locking member rotates in a second direction, or the plunger rotates in a first direction, or both, wherein, optionally, (i) upon rotation of the locking member in the second direction, or the plunger in the first direction, or both, the locking member interfaces with the plunger to lock the plunger in a retracted position, and (ii) wherein the tab of the locking member interfaces with the plunger to maintain the plunger in the retracted, locked position until reset.

9. The nasal drug delivery training device of claim 8, wherein the plunger is reset by rotation of the plunger, removing the interaction between the tab and the rail, and extending the plunger.

10. The nasal drug delivery training device of claim 9, wherein (i) the plunger biasing member causes extension of the plunger, and (ii) the plunger is rotated in the first direction to initiate reset of the device.

11. The nasal drug delivery training device of claim 2, further comprising a reset member for interfacing with the nasal drug delivery device to unlock the device.

12. The nasal drug delivery training device of claim 11, wherein the reset member comprises a proximal end and a distal end, wherein a gripping portion is positioned at the distal end, and an elongated portion extends therefrom, toward the proximal end of the reset member.

13. The nasal drug delivery training device of claim 12, wherein the proximal end of the reset member comprises a plunger interfacing tip for interfacing with the plunger via the cavity in the device, such that movement of the distal end of the reset member inside the aperture against the plunger resets the plunger.

14. The nasal drug delivery training device of claim 2, further comprising a reset button disposed on a portion of the housing, wherein the plunger is reset to an extended position by actuation of the reset button.

15. The nasal drug delivery training device of claim 11, wherein the reset member comprises a receiving device for receiving at least a portion of the nasal drug delivery training device, wherein upon receipt of a portion of the nasal drug delivery training device within the reset member, the nasal drug delivery training device is reset from a post use position to a pre-use position, wherein, optionally, (i) in a post use position, the plunger is in the retracted position, and in a pre-use position, the plunger is in an extended position, (ii) the receiving device comprises a receiving device housing defining a vesicle for receiving the portion of the nasal drug delivery training device, (iii) the portion of the nasal drug delivery training device to be received within the receiving device comprises the nasal interfacing portion, and (iv) the portion of the nasal drug delivery training device to be received within the receiving device comprises the distal portion of the device.

16. The nasal drug delivery training device of claim 5, wherein the housing further comprises a retainer member, wherein, optionally, (i) the retainer member comprises a retainer member opening for receiving the plunger, (ii) the retainer member is configured to receive at least a portion of the torsion spring, and (iii) the retainer member comprises a ramp portion configured to interface with the plunger rail during extension of the plunger.

17. The nasal drug delivery training device of claim 7, wherein the plunger further comprises a flange, said flange interfaces with the locking member when the plunger is in the extended position.

18. The nasal drug delivery training device of claim 17, wherein the locking member tab first surface abuts the flange when the plunger is in the extended position.

19. The nasal drug delivery training device of claim 7, wherein the tab second surface comprises an angled surface, wherein, optionally, the angled surface comprising an angle of less than 20 degrees.

20. The nasal drug delivery training device of claim 7, wherein the interface between the rail and the tab second surface simulates a nasal drug delivery device break-out force as the plunger moves from an extended position following actuation of the device.

21. The nasal drug delivery training device of claim 20, wherein the break-out force comprises a force between 0.001 Newtons and 46 Newtons.

* * * * *